US006303749B1

(12) United States Patent
Jarosinski

(10) Patent No.: US 6,303,749 B1
(45) Date of Patent: Oct. 16, 2001

(54) AGOUTI AND AGOUTI-RELATED PEPTIDE ANALOGS

(75) Inventor: Mark Anthony Jarosinski, Boulder, CO (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/240,078

(22) Filed: Jan. 29, 1999

(51) Int. Cl.$^7$ ................................ C07K 9/00; C07K 7/08

(52) U.S. Cl. .................... 530/300; 530/324; 530/326; 530/328; 530/345

(58) Field of Search ................................ 530/300, 350, 530/345, 324, 326, 328

(56) References Cited

U.S. PATENT DOCUMENTS

| | | |
|---|---|---|
| 3,773,919 | 11/1973 | Boswell et al. . |
| 4,376,110 | 3/1983 | David et al. . |
| 4,816,567 | 3/1989 | Cabilly et al. . |
| 4,892,538 | 1/1990 | Aebischer et al. . |
| 5,011,472 | 4/1991 | Aebischer et al. . |
| 5,106,627 | 4/1992 | Aebischer et al. . |
| 5,252,714 | 10/1993 | Harris et al. . |
| 5,653,975 | 8/1997 | Baetge et al. . |

FOREIGN PATENT DOCUMENTS

| | | |
|---|---|---|
| 0 036676 | 9/1981 | (EP) . |
| 0 058 481 | 8/1982 | (EP) . |
| 0 088046 | 9/1983 | (EP) . |
| 0 133 988 | 3/1985 | (EP) . |
| 0 143 949 | 6/1985 | (EP) . |
| 0 154 316 | 9/1985 | (EP) . |
| 0 401 384 | 12/1990 | (EP) . |
| WO 91/10425 | 7/1991 | (WO) . |
| WO 97/43412 | 11/1997 | (WO) . |
| WO 99/43709 | 9/1999 | (WO) . |

OTHER PUBLICATIONS

Bowie et al. Science 247:1306–1310, 1990.*
Wells. Biochemistry 29:8509–8510, 1990.*
Ngo et al. The Protein Folding Problem and Tertiary Structure Prediction, Merz et al., eds., Birkhauser, Boston, pp. 492–495, 1994.*
Bodi et al., "New Strategy for th Synthesis of Large Peptides as Applied to the C–terminal Cystein–Rich 41 Amino Acid Fragment of the Mouse Agouti Protein," *Tetrahedon Letters*, 38(18): 3293–3296 (1997).
Yang et al., "Characterization of Agouti–Related Protein Binding to Melanocortin Receptors," *Molecular Endocrinology* 13(1): 148–155 (1999).
Atschul, et al., *Journal of Molecular Biology*, 215: 403–410 (1990).
Bayer, et al., *Meth. Enz.*, 184: 138–163 (1990).
Brodeur, et al., "Mouse–Human Myeloma Partners for the Production of Heterohybridomas", Monoclonal Antibody Production Techniques and Applications, Chapter 4, pp. 51–63, Marcel Dekker, Inc., New York (1987).
Bruggermann, et al., Year in Immuno., 7:33 (1993).
Bures, et al., "Determination of Disulfide Structure in Agouti–Related Protein (AGRP) by Stepwise Reduction and Alkylation", *Biochemistry*, 37: No. 35, pp. 12172–12177 (1998).
Bultman, et al., *Cell*, 71: 1195–1204 (1992).
Cahn, et al., Pure Applied Chemistry, 45: 11–30 (1974).
Carillo, et al., *SIAM Journal Applied Mathematics*, 48: 1073 (1988).
David, et al., *Biochemistry*, 13: 1014–1021 (1974).
Devereux, et al., *Nucleic Acids Research*, 12(1): 387 (1984).
Engels, et al., *Angew. Chem. Intl. Ed.*, 28: 716–734 (1989).
Eppstein, et al., *Proc. Natl. Acad. Sci. USA*, 82: 3688–3692 (1985).
Fong, et al., "ART (Protein Product of Agouti–Related Transcript) as an Antagonist of MC–3 and MC–4 Receptors", Biochemical and Biophysical Research Communications, 237: pp. 629–631, (1997).
Greene, et al., Protective Groups in Organic Synthesis, 2d. ed., John Wiley and Sons (1991).
Hoogenboom, et al., *J. Mol. Biol.*, 227: 381 (1991).
Houghten, et al., Proc. Natl. Acad. Sci. USA, 82: 5132 (1985).
Jakobovits, et al., Proc. Natl. Acad. Sci., 90: 2551–2555 (1993).
Jakobovits, et al., Nature, 362: 255–258 (1993).
Jones, et al., Nature, 332: 522–525 (1986).
Kiefer, et al., "Melanocortin Receptor Binding Determinants in the Agouti Protein", *Biochemistry*, 37: pp. 991–997, (1998).
Kitts, et al., *Biotechniques*, 14: 810–817 (1993).
Kohler, et al., "Continuous cultures of fused cells secreting antibody of predefined specificity", *Naturee*, 256:495–497 (1975).
Kozbor, *J. Immunol.*, 133: 3001 (1984).
Langer, et al., *J. Biomed. Mater. Res.*, 15: 167–277 (1981).
Langer, et al., *Chem. Tech.*, 12: 98–105 (1982).
Lucklow, *Curr. Opin. Biotechnol.*, 4: 564–572 (1993).
Lucklow, et al., *Journal of Virology*, 67: 4566–4579 (1993).
Marks, et al., *J. Mol. Biol.*, 222: 581 (1991).
Marston, et al., *Meth. Enz.*, 182: 264–275 (1990).
Merrifield, et al., *J. Am. Chem. Soc.*, 85: 2149 (1963).
Morrison, et al., Proc. Natl. Acad. Sci. USA, 81: 6851–6855 (1985).

(List continued on next page.)

Primary Examiner—Elizabeth Kemmerer
(74) Attorney, Agent, or Firm—Nancy A. Oleski; Ron K. Levy; Steven M. Odre

(57) ABSTRACT

The present invention provides peptides related to agouti signaling protein and agouti related protein which are useful in modulating the activity of the melanocortin 3 and melanocortin 4 receptors. Also provided are methods of preparing the peptides, as well as nucleic acid molecules encoding the peptides.

4 Claims, No Drawings

OTHER PUBLICATIONS

Ollmann, et al., "Antagonism of Central Melanocortin Receptors in Vitro and in Vivo by Agouti–Related Protein", *Science*, 278: pp. 135–138, (1997).

Pain, et al., *J. Immunol. Meth.*, 40: 216–231 (1982).

Perry, et al., "Coupled Site–Directed Mutagenesis/Transgenesis Identifies Important Functional Domains of the Mouse Agouti Protein", *Genetics*, 144: pp. 255–264, (1996).

Quillan, et al., "A synthetic human Agouti–related protein (83–132)–$NH_2$ fragment is a potent inhibitor of melanocortin receptor function", *FEBS Letters*, 428: pp. 59–62, (1998).

Riechmann, et al., *Nature*, 332: 323–327 (1988).

Rossi, et al., "A C–terminal fragment of Agouti–related protein increases feeding and antagonizes the effect of alpha–melanocyte stimulating hormore in vivo", *Endocrinology*, 139, No. 10: pp. 4428–4431 (1998).

Shutter, et al., "Hypothalamic expression of ART, a novel gene related to agouti, is up–regulated in obese and diabetic mutuant mice", *Genes and Development*, 11: pp. 593–602, (1997).

Sidman, et al., *Biopolymers*, 22: 547–556 (1983).

Sola, "Using Monoclonal Antibodies: Soluble Antigens", *Monoclonal Antibodies: A Manual of Techniques*, Chapter 6, pp. 147–158, CRC Press, Inc., (1987).

Stark, "Agrp, a novel gene implicated in the control of feeding", *Exp. Opin. Invest. Drugs*, 7(6): pp. 859–864 (1998).

Tota, et al., "Molecular Interaction of Agouti Protein and Agouti–Related Protein with Human Melanocortin Receptors", *Biochemistry*, 38, No. 3: pp. 897–904, (1999).

Verhoeyen, et al., *Science*, 239: 1534–1536 (1988).

Willard, et al., "Agouti Structure and Function: Characterization of a Potent α–Melanocyte Stimulating Hormone Receptor Antagonist", *Biochemistry*, 34: pp. 12341–12346, (1995).

IUPAC–IUB Joint Commission on Biochemical Nomenclature, *Biochem. J.*, 219: 345–373 (1984).

* cited by examiner

AGOUTI AND AGOUTI-RELATED PEPTIDE ANALOGS

BACKGROUND

1. Field of the Invention

This invention relates to peptide analogs of agouti polypeptide and agouti-related polypeptide that are useful in modulating feeding behavior.

2. Related Art

Obesity is now recognized as a major health problem due in part to the association of obesity with cardiovascular disease, hypertension, and type II diabetes (Stark, *Exp. Opin. Invest. Drugs*, 7:859–864 [1998]). Obesity is believed to result from the interaction of several genetic and environmental factors. Several genes have recently been identified as having a role in feeding behavior. Some of these genes are leptin, carboxypeptidase, tubby, and agouti (Stark, supra).

The agouti gene was cloned in 1992 and was found to encode a 131 amino acid polypeptide (Bultman et al., *Cell*, 71:1195–1204). The human agouti polypeptide is commonly referred to as agouti signaling protein, or "ASP". Recent research has demonstrated that ASP binds to melanocortin-1 receptor and melanocortin-4 receptor (Stark, supra). Various attempts have been made to identify the amino acid residues of ASP that are important for binding. An ASP carboxy-terminal peptide encompassing amino acids 83–131 has been generated via expression cloning and is purportedly as active as full length ASP (Willard et al., *Biochem.*, 34:12341–12346 [1995]). Several ASP amino acid variants have been prepared by expression cloning methods. For example, Kiefer et al. (*Biochem.*, 37:991–997 [1998]) have prepared various Ala scan mutants, and Perry et al. (*Genetics*, 144:255–264 [1996]) have prepared two deletion mutants (desArg5-Phe14 and desArg64-Lys77) as well as various Arg, Ser and Asp substitution mutants.

Agouti related polypeptide (also referred to as "AGRP") is known to affect feeding behavior. Mice injected with AGRP peptides have been shown to increase their food uptake, resulting in obesity and diabetes (Stark, supra). Recent research suggests that AGRP is purportedly an antagonist of melanocortin-3 receptor and melanocortin-4 receptor (Fong et al., *Biochim. Biophys. Res. Comm.*, 237:629–631 [1997]; Ollmann et al., *Science*, 278:135–138 [1997]). These melanocortin receptors have been implicated in weight regulation (Ollmann et al., supra).

The gene encoding human AGRP has been cloned and sequenced (Shutter et al., *Genes Dev.*, 11:593–602 [1997]). The corresponding human polypeptide is 132 amino acids in length, and is about 25 percent identical to human agouti polypeptide. Human AGRP contains 11 cysteines, the majority of which are located at the carboxy terminal end of the polypeptide, and form 5 disulfide bridges (Bures et al., *Biochemistry*, 37:12172–12177 [1998]).

In an effort to identify the active region of AGRP polypeptide, various peptides of the full length molecule have been prepared and tested for activity. PCT patent application WO 97/43412 (published Nov. 20, 1997) describes an AGRP peptide of amino acids 79–132. Rossi et al. (*Endocrinology*, 139:4428–4431 [1998]) describe production of the AGRP peptide 83–132. Quillan et al. (*FEBS Lett.*, 428:59–62 [1998]) describe production of the AGRP peptide 83–132, AGRP peptide 25–51, and AGRP peptide 54–82 using solid phase synthesis methods. Bures et al., supra, describe several AGRP peptides prepared by proteolytic digestion of full length recombinant AGRP including AGRP 102–112, 70–89, 90–92, 97–106, 105–112, 106–112, 75–91, 96–97, 75–91, 70–74, 64–67, 96–101, and 98–101.

In view of the need to better understand the biology of obesity, there is a need to identify and develop novel agonist and/or antagonist ligands of the melanocortin-3 and melanocortin-4 receptor subtypes with increased differential selectivity as compared with AGRP and ASP.

Accordingly, it is an object of this invention to provide molecules that can modulate, either positively or negatively, the biological activity of AGRP and ASP. This and other objects will be readily apparent to one of ordinary skill in the art.

SUMMARY OF THE INVENTION

In one aspect, the present invention provides a peptide selected from the group consisting of:

(a) the peptide of any of SEQ ID NOs:1–26;

(b) a peptide encoded by a nucleic acid molecule wherein the complement of the nucleic acid molecule hybridizes to any of the nucleic acid molecules of SEQ ID NOs: 27–52 under conditions of high stringency; and (c) a peptide containing one or more conservative amino acid substitutions as compared to any of the peptides of SEQ ID NOs:1–26.

Optionally, such peptides may be acylated at the amino terminus, and an acetyl group may be used for acylation.

In another embodiment, the present invention provides an isolated nucleic acid molecule selected from the group consisting of:

(a) the nucleic acid molecule of any of SEQ ID NOs:27–52;

(b) the complement of a nucleic acid molecule that hybridizes under conditions of high stringency to any of SEQ ID NOs: 27–52; and (c) a nucleic acid molecule encoding a peptide that contains one or more conservative amino acid substitutions as compared to the peptides of any of SEQ ID NOs: 1–26.

The invention further provides a vector comprising any of such nucleic acid molecules, as well as eukaryotic and prokaryotic host cells comprising such vectors.

DETAILED DESCRIPTION OF THE INVENTION

The section headings herein are for organizational purposes only and are not to be construed as limiting in any way the subject matter described therein.

Definitions

The term "AGRP/ASP peptides" refers to the peptides having the amino acid sequence of any of SEQ ID NOs:1–26, together with all related peptides described herein. Related peptides includes allelic variants, fragments, derivatives, substitution, deletion, and insertion variants, fusion polypeptides, and orthologs, and each amino acid of each such related peptide may be of the "D" (natural) or "L" (unnatural) configuration which corresponds to the stereochemical designation "S" and "R", respectively, as defined in the RS system of Cahn et al. (*Pure Applied Chemistry*, 45:11–30, [1974], and references therein). Such related peptides may be mature peptides, i.e., lacking a signal peptide. The AGRP/ASP peptides may or may not have amino terminal methionines, depending on the manner in which they are prepared.

As used herein, the term "AGRP/ASP peptide variants" refers to AGRP/ASP peptides whose amino acid sequences contain one or more amino acid sequence substitutions, deletions, and/or additions as compared to the AGRP/ASP peptide amino acid sequences set forth in SEQ ID NOS:1–26. Such AGRP/ASP peptide variants containing amino acids of the natural L-configuration can be prepared from the corresponding AGRP/ASP nucleic acid molecule variants, which have a DNA sequence that varies accordingly from the DNA sequences encoding the wild type AGRP/ASP peptides as set forth in SEQ ID NOS:1–26. Alternatively, such variants containing amino acids of the D-configuration (unnatural form) can be prepared synthetically using standard methods described herein (see also *Biochem. J.*, 219:345–373 [1984]).

As used herein, the term "AGRP/ASP peptide derivatives" refers to AGRP/ASP peptides, variants, or fragments thereof, that have been chemically modified, as for example, by addition of one or more water soluble polymers, N-linked or O-linked carbohydrates, sugars, phosphates, and/or other such molecules, where the molecule or molecules are not naturally attached to wild-type AGRP/ASP peptides. Derivatives further includes deletion of one or more chemical groups naturally attached to the AGRP/ASP peptide.

As used herein, the terms "biologically active AGRP/ASP peptides", "biologically active AGRP/ASP peptide fragments", "biologically active AGRP/ASP peptide variants", and "biologically active AGRP/ASP peptide derivatives" refer to AGRP/ASP peptides which bind to both the human melanocortin-3 receptor and to the human melanocortin-4 receptor, and have a binding affinity to one of these receptors when competed against $I^{-125}$AGRP of no greater than 1000 nM.

As used herein, the term "AGRP/ASP nucleic acid molecule" when used to describe a nucleic acid molecule refers to a nucleic acid molecule or fragment thereof that encodes any of the AGRP/ASP peptides of SEQ ID NOs:1–26, and any fragments, derivatives, substitution, deletion, and insertion variants, fusion peptides, fusion polypeptides, and orthologs thereof.

"Identity," as known in the art, is a relationship between the sequences of two or more peptide molecules or two or more nucleic acid molecules, as determined by comparing the sequences. In the art, "identity" also means the degree of sequence relatedness between peptide or nucleic acid molecule sequences, as the case may be, as determined by the match between strings of nucleotide or amino acid sequences. "Identity" measures the percent of identical matches between two or more sequences with gap alignments addressed by particular computer programs (i.e., "algorithms").

"Similarity" is a related concept, but in contrast to "identity", a measure of similarity includes both identical matches and conservative substitution matches. Since conservative substitutions apply to peptides and not nucleic acid molecules, similarity only deals with peptide sequence comparisons. If two peptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two peptide sequences will be higher than the percent identity between those two sequences.

"Conservative" amino acid substitutions are described herein below in reference to Table I. Based on Table I, conservative amino acid substitutions are alternate amino acids selected from the same grouping, e.g., basic, acidic, uncharged polar, and non-polar. For example, conservative amino acid substitutions for arginine would be lysine and histidine.

Identity and similarity can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 19933; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991; and Carillo, H., and Lipman, D., *SIAM J. Applied Math.*, 48:1073 (1988).

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux, J., et al., *Nucleic Acids Research* 12(1):387 (1984); Genetics Computer Group, University of Wisconsin, Madison, Wis.), BLASTP, BLASTN, and FASTA (Atschul, S. F. et al., *J. Molec. Biol.* 215:403–410 (1990). The BLAST X program is publicly available from the National Center for Biotechnology Information (NCBI) and other sources (BLAST Manual, Altschul, S., et al. NCB NLM NIH Bethesda, Md. 20894; Altschul, S., et al., *J. Mol. Biol.* 215:403–410 (1990). The well known Smith Waterman algorithm may also be used to determine identity.

By way of example, using the computer algorithm GAP (Genetics Computer Group, University of Wisconsin, Madison, Wis.), two peptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., in: Atlas of Protein Sequence and Structure, vol. 5, supp.3 [1978] for the PAM250 comparison matrix; see Henikoff et al., *Proc. Natl. Acad. Sci USA*, 89:10915–10919 [1992] for the BLOSUM 62 comparison matrix) is also used by the algorithm.

Preferred parameters for peptide and polypeptide sequence comparison include the following:

Algorithm: Needleman and Wunsch, *J. Mol. Biol.* 48:443–453 (1970)

Comparison matrix: BLOSUM 62 from Henikoff and Henikoff, *Proc. Natl. Acad. Sci. USA* 89:10915–10919 (1992)

Gap Penalty: 12

Gap Length Penalty: 4

Threshold of Similarity: 0

The GAP program is useful with the above parameters. The aforementioned parameters are the default parameters for peptide and polypeptide comparisons (along with no penalty for end gaps) using the GAP algorithm.

Preferred parameters for nucleic acid molecule sequence comparison include the following:

Algorithm: Needleman and Wunsch, *J. Mol Biol.* 48:443–453 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will depend on the specific comparison whether it is peptide to protein, peptide to peptide, protein to DNA; and additionally, whether the comparison is between pairs of sequences (in which case GAP or BestFit are generally preferred) or between one sequence and a large database of sequences (in which case FASTA or BLASTA are preferred).

Peptides or polypeptides that are at least 70 percent identical will typically have one or more amino acid substitutions, deletions, and/or additions as compared with any of the wild type AGRP/ASP polypeptides. Usually, the substitutions of the native residue will be either alanine, or a conservative amino acid so as to have little or no effect on the overall net charge, polarity, or hydrophobicity of the polypeptide. Conservative substitutions are set forth in Table I below.

TABLE I

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | norleucine |
| | isoleucine |

For each amino acid, an additional conservative substitution includes the "homolog" of that amino acid, where the "homolog" is an amino acid with a methylene group (CH2) inserted into the side chain at the beta position of that side chain. Examples of such homologs include, without limitation, homophenylalanine, homoarginine, homoserine, and the like.

The term "ortholog" refers to an AGRP/ASP peptide that corresponds to an AGRP/ASP peptide obtained from a species other than that from which an AGRP/ASP peptide of any of SEQ ID NOs:1–26 was obtained.

The term "allelic variant" refers to one of several possible naturally occurring alternate forms of a gene occupying a given locus on a chromosome of an organism.

The term "mature amino acid sequence" refers to a polypeptide or peptide lacking a signal peptide.

The term "isolated nucleic acid molecule" refers to a nucleic acid molecule that is free from at least one contaminating nucleic acid molecule with which it is naturally associated, and preferably substantially free from any other contaminating mammalian nucleic acid molecules.

The terms "isolated AGRP/ASP polypeptide and isolated AGRP/ASP peptide" refer to an AGRP/ASP polypeptide or AGRP/ASP peptide that is free from at least one contaminating polypeptide or peptide that is found in the natural environment of the AGRP/ASP peptide or polypeptide, and preferably is substantially free from any other contaminating mammalian polypeptides.

Nucleic acid molecules that hybridize to the nucleic acid molecules of SEQ ID NOs: 27–52, as well as their complements, are also contemplated as part of this invention. Such hybridization can be conducted under conditions of moderate or high stringency as described below. Preferably, the nucleic acid molecules are those that hybridize under conditions of high stringency.

"High stringency conditions" are those that (1) employ low ionic strength and high temperature for washing, for example, 0.015 M NaCl/0.0015 M sodium citrate/0.1% NaDodSO4 (SDS) at 50° C., or (2) employ during hybridization a denaturing agent such as formamide, for example, 50% (vol/vol) formamide with 0.1% bovine serum albumin/0.1%. Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

"Moderate stringency conditions" are described in Sambrook et al., infra, and include the use of a washing solution and hybridization conditions (e.g., temperature, ionic strength, and % SDS) less stringent than described above. An example of moderately stringent conditions are conditions such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μl/ml denatured sheared salmon sperm DNA, followed by washing the filters in 1×SSC at about 37–50° C. The skilled artisan will recognize how to adjust the temperature, ionic strength etc. as necessary to accommodate factors such as probe length and the like.

Where oligonucleotide probes are used to screen cDNA or genomic libraries, one of the following two high stringency solutions may be used. The first of these is 6×SSC with 0.05 percent sodium pyrophosphate at a temperature of 35° C.–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second high stringency solution utiLizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

As used herein, the terms "effective amount" and "therapeutically effective amount" refer to the amount of a AGRP/ASP polypeptide necessary to support one or more biological activities of the AGRP/ASP polypeptides as set forth above.

Nucleic Acid Molecules

The invention encompasses nucleic acid molecules encoding AGRP/ASP peptides. Such nucleic acid molecules can be prepared using the following exemplary methods.

A full-length AGRP/ASP polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds., (*Current Protocols in Molecular Biology*, Green Publishers Inc. and Wiley and Sons, NY [1994]).

A gene or CDNA encoding an AGRP/ASP polypeptide or fragment thereof may be obtained by hybridization screening of a genomic or cDNA library, or by PCR amplification. Probes or primers useful for screening a library by hybridization can be generated based on sequence information for other known genes or gene fragments from the same or a related family of genes, such as, for example, conserved motifs. In addition, where a gene encoding AGRP/ASP polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the AGRP/ASP gene. Typically, conditions of moderate or high stringency, as described above, will be employed for screening to minimize the number of false positives obtained from the screen. Once a clone has been obtained, it can be sequenced using standard methods well known in the art to confirm that it is indeed an AGRP/ASP polypeptide.

In one embodiment, an AGRP/ASP cDNA or gene can be cut using the appropriate restriction endonucleases to generate a DNA fragment that encodes certain AGRP/ASP peptides of the present invention (i.e., those that are native sequences having no amino acid substitutions or deletions). Such fragments can then be used to generate the AGRP/ASP peptide variants of the present invention using methods described herein.

Another means to prepare a nucleic acid molecule encoding an AGRP/ASP peptide or fragment thereof is to employ chemical synthesis using methods well known to the skilled artisan such as those described by Engels et al.(Angew. Chem. Intl. Ed., 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry.

In some cases, it may be desirable to prepare nucleic acid and/or amino acid variants of the naturally occurring AGRP/ASP peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce the AGRP/ASP polypeptide(s). Such "codon optimization" can be determined via computer algorithms which incorporate codon frequency tables such as "Ecohigh. Cod" for codon preference of highly expressed bacterial genes as provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high.cod". Still other preferred variants are those encoding one or more amino acid substitutions in which alanine is substituted for the naturally occurring amino acid(S), and those encoding conservative amino acid changes as described above (e.g., wherein the charge or polarity of the naturally occurring amino acid side chain is not altered substantially by substitution with a different amino acid) as compared to wild type AGRP/ASP peptides.

The nucleic acid molecule encoding the AGRP/ASP peptide can be inserted into an appropriate expression or amplification vector using standard ligation techniques. The vector is typically selected to be functional in the particular host cell employed (i.e., the vector is compatible with the host cell machinery such that amplification of the gene and/or expression of the gene can occur). The nucleic acid molecule encoding the AGRP/ASP peptide may be amplified/expressed in prokaryotic, yeast, insect (baculovirus systems) and/or eukaryotic host cells. Selection of the host cell will depend in part on whether the AGRP/ASP peptide is to be post-translationally modified. If so, yeast, insect, or mammalian host cells are preferable.

Typically, the vectors used in any of the host cells will contain 5' flanking sequence (also referred to as a "promoter"), as well as other regulatory elements such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below.

Optionally, the vector may contain a "tag" sequence, i.e., an oligonucleotide molecule located at the 5' or 3' end of the AGRP/ASP peptide coding sequence; the oligonucleotide molecule encodes polyHis (such as hexaHis), or other "tag" such as FLAG, HA (hemaglutiniri Influenza virus) or myc for which commercially available antibodies exist. This tag is typically fused to the polypeptide upon expression of the polypeptide, and can serve as means for affinity purification of the AGRP/ASP peptide from the host cell. Affinity purification can be accomplished, for example, by column chromatography using antibodies against the tag as an affinity matrix. Optionally, the tag can subsequently be removed from the purified AGRP/ASP peptide by various means such as using certain peptidases for cleavage.

The 5' flanking sequence may be obtained from the same species and/or strain as the host cell (homologous), or may be from a species other than the host cell species or strain (heterologous), hybrid (i.e., a combination of 5' flanking sequences from more than one source), synthetic, or it may be the native AGRP/ASP gene 5' flanking sequence. As such, the source of the 5' flanking sequence may be any unicellular prokaryotic or eukaryotic organism, any vertebrate or invertebrate organism, or any plant, provided that: the 5' flanking sequence is functional in, and can be activated by, the host cell machinery.

The 5' flanking sequences useful in the vectors of this invention may be obtained by any of several methods well known in the art. Typically, 5' flanking sequences useful herein other than the AGRP/ASP gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the AGRP/ASP peptide. If the vector of choice does not contain an origin of replication site, one may be chemically synthesized based on a known sequence, and ligated into the vector.

The transcription termination element is typically located 3' of the end of the AGRP/ASP polypeptide coding sequence and serves to terminate transcription of the AGRP/ASP polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, characterized by having a Shine-Dalgarno sequence (prokaryotes) or a Kozak sequence (eukaryotes), is usually necessary for translation initiation of mRNA. The element is typically located 3' to the promoter and 5' to the coding sequence of the AGRP/ASP peptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A signal sequence may be used to direct the AGRP/ASP peptide out of the host cell where it is synthesized. Typically, the signal sequence is positioned in the coding region of the AGRP/ASP DNA, or directly at the 5' end of the AGRP/ASP DNA coding region. Many signal sequences have been identified, and any of them that are functional in the selected host cell may be used in conjunction with the AGRP/ASP DNA. Therefore, the signal sequence may be homologous (naturally occurring) or heterologous to the AGRP/ASP DNA. Additionally, the signal sequence may be chemically synthesized using methods set forth above.

In most cases, secretion of the AGRP/ASP peptide from the host cell via the presence of a signal peptide will result in the removal of the signal peptide from the AGRP/ASP peptide.

In many cases, transcription of the AGRP/ASP DNA is increased by the presence of one or more introns in the vector; this is particularly true where the AGRP/ASP peptide is produced in eukaryotic host cells, especially mammalian host cells. The introns used may be naturally occurring within the AGRP/ASP DNA, especially where the DNA used is a full length genomic sequence or a fragment thereof. Where the intron is not naturally occurring within the gene (as for most cDNAs), the intron(s) may be obtained from another source. The position of the intron with respect to the 5' flanking sequence and the AGRP/ASP DNA is generally important, as the intron must be transcribed to be effective. As such, where the AGRP/ASP DNA inserted into the expression vector is a cDNA molecule, the preferred position for the intron is 3' to the transcription start site, and 5' to the polyA transcription termination sequence. Preferably for AGRP/ASP DNA, the intron or introns will be located on one side or the other (i.e., 5' or 3') of the DNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII, pCR3, and pcDNA3.1 (Invitrogen Company, San Diego, Calif.), PBSII (Stratagene Company, La Jolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha, and pFastBacDual (Gibco/BRL, Grand Island, N.Y.).

After the vector has been constructed and a nucleic acid molecule encoding AGRP/ASP peptide has been inserted into the proper site of the vector, the completed vector may be inserted into a suitable host cell for amplification and/or polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize AGRP/ASP polypeptide which can subsequently be collected from the culture medium (if the host cell secretes it into the medium) or directly from the host cell producing it (if it is not secreted).

Selection of the host cell for AGRP/ASP peptide production will depend upon a number of factors, such as, for example, whether the polypeptide is to be secreted from the host cell, whether the peptide is to be post-translationally modified, and whether the peptide is to be recovered from the culture medium in a folded form (three-dimensional structure).

Suitable host cells or cell lines may be mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5a, DH10, and MC1061) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Preferred yeast cells include, for example, *Saccharomyces cerivisae*.

Additionally, where desired, insect cell systems may be utilized in the methods of the present invention. Such systems are described for example in Kitts et al. (*Biotechniques*, 14:810–817 [1993]), Lucklow (*Curr. Opin. Biotechnol.*, 4:564–572 [1993])and Lucklow et al. (*J. Virol.*, 67:4566–4579 [1993]). Preferred insect cells are Sf-9 and Hi5 (Invitrogen, Carlsbad, Calif.).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

AGRP/ASP Peptide Production

The host cells containing the vector (i.e., transformed or transfected) may be cultured using standard media. well known to the skilled artisan. The media will usually contain all nutrients necessary for the growth and. survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of AGRP/ASP peptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the AGRP/ASP peptide has been designed to be secreted from the host cells, the majority of peptide may be found in the cell culture medium. If however, the AGRP/ASP peptide is not secreted from the host cells, it will be present in the cytoplasm and/or the nucleus (for eukaryotic host cells) or in the cytosol (for gram negative bacteria host cells).

For AGRP/ASP peptide situated in the host cell cytoplasm and/or nucleus, the host cells are typically first disrupted mechanically or with detergent to release the intra-cellular contents into a buffered solution. AGRP/ASP peptide can then be isolated from this solution.

Purification of AGRP/ASP peptide from solution can be accomplished using a variety of techniques. If the peptide has been synthesized such that it contains a tag such as Hexahistidine (AGRP/ASP peptide/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing AGRP/ASP peptide). For example, polyhistidine binds with great affinity and specificity to nickel, thus an affinity column of nickel (such as the Qiagen® nickel columns) can be used for purification of AGRP/ASP peptide/polyHis. (See for example, Ausubel et al., eds., *Current Protocols in Molecular Biology*, Section 10.11.8, John Wiley & Sons, New York [1993]).

Where the AGRP/ASP polypeptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the AGRP/ASP peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If the AGRP/ASP peptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The AGRP/ASP peptide in its now soluble form can then be analyzed using gel electrophoresis, immunoprecipitation or the like. If it is desired to isolate the AGRP/ASP peptide, isolation may be accomplished using standard methods such as those set forth below and in Marston et al. (*Meth. Enz.*, 182:264–275 [1990]). In some cases, the AGRP/ASP peptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a chaotropic agent, where the chaotropic agent can be selected from those listed above. In most cases the refolding/oxidation solution will also contain a reducing agent and the reducing agent in its oxidized form in a specific ratio to generate a particular redox potential allowing for disulfide shuffling to occur in the formation of cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol(bME)/dithio-b(ME). In many instances a co-solvent is necessary to increase the efficiency of the refolding. The more common reagents used for this purpose include glycerol, polyethylene glycol of various molecular weights, and arginine.

If AGRP/ASP ppeptide inclusion bodies are not formed to a significant degree in the host cell, the AGRP/ASP peptide will be found primarily in the supernatant after centrifugation of the cell homogenate, and the AGRP/ASP peptide can be isolated from the supernatant using methods such as those set forth below.

In those situations where it is preferable to partially or completely isolate the AGRP/ASP peptide, purification can be accomplished using standard methods well known to the skilled artisan. Such methods include, without limitation, separation by electrophoresis followed by electroelution, various types of chromatography (affinity, immunoaffinity, molecular sieve, and/or ion exchange), and/or high pressure liquid chromatography. In some cases, it may be preferable to use more than one of these methods for complete purification.

In addition to preparing and purifying AGRP/ASP peptide using recombinant DNA techniques, the AGRP/ASP peptides, variants, fragments and derivatives thereof may be prepared by chemical synthesis methods such as solid phase peptide synthesis using techniques known in the art such as those set forth by Merrifield et al., (*J. Am. Chem. Soc.*, 85:2149 [1963]), Houghten et al. (*Proc Natl Acad. Sci. USA*, 82:5132 [1985]), Stewart and Young (Solid Phase Peptide Synthesis, Pierce Chemical Co., Rockford, Ill. [1984]), Bodanszky et al., (The Practice of Peptide Synthesis, Springer-Verlag, Berlin, Germany [1984]), and Gross and Meinhofer, eds, (The Peptides, Academic Press [1979] vol. I–III). Chemical synthesis of the peptides of the present invention is the preferred method of preparation of these peptides.

Typically, the peptides of the present invention are synthesized from readily available starting materials. Synthesis is usually conducted from carboxy to amino terminus. During synthesis, the alpha- amine of the amino acid to be added is protected by a urethane such as Boc, Cbz, Fmoc, or Alloc (see Greene et al., *Protective Groups in Organic Synthesis*, 2d. ed., John Wiley and Sons [1991] for a list of protective groups) while the free carboxyl is activated with an activating reagent which is usually a carbodiimide such as DCC (Dicyclohexyl carbodiimide), EDC (1-(3-dimethylaminopropyl)-3-ethylcarbodiimide), or DIC (diisopropylcarbodiimide). A preferred protective group is Fmoc. The activating reagent can optionally be used in the presence of a catalyst such as Hobt (N-Hydroxybenzotriazole) Hoat (7-aza-N-hydroxybenzotriazole), Hosu, or Dmap (Dimethylaminopyridine). After the peptide is completely synthesized, the side chain protecting groups may be removed using methods set forth in the above cited references. Such methods include, without limitation, hydrogenation in the presence of a catalyst such as palladium, platinum, or rhodium; treatment with sodium in liquid ammonia, hydrochloric, hydrofluoric, hydrobromic, formic, trifluoromethanesulfonic, or trifluoroacetic acid; secondary amines; fluoride ion; trimethylsilyl halides such as bromide and iodide; or alkali.

The above described methods may be accomplished manually or using an automated peptide synthesizer such as an Applied Biosystems model 430, 430A, A431, A433 and using programming modules as defined by the manufacture manuals.

Chemically synthesized AGRP/ASP peptides or fragments may be oxidized to permit the formation of disulfide bridges using standard methods set forth in the above cited references.

The AGRP/ASP peptides or fragments are expected to have biological activity comparable to AGRP/ASP peptides produced recombinantly and thus may be used interchangeably with recombinant or AGRP/ASP peptide.

AGRP/ASP Peptides

Included in the scope of the present invention are isolated AGRP/ASP peptides, fragments, variants, fusion polypeptides, and derivatives thereof as defined herein.

AGRP/ASP fragments encompassed by this invention may be truncated at the amino terminus, the carboxy terminus, and/or internal deletion as compared with full length AGRP/ASP peptides. Such AGRP/ASP fragments may be prepared with or without an amino terminal methionine.

Preferred AGRP/ASP variants include those having one or more conservative amino acid substitutions as compared to any of the AGRP/ASP peptides of SEQ ID NOs:1–26, as well as those variants having one or more alanine substitutions as compare with any of the AGRP/ASP peptides of SEQ ID NOs:1–26.

Preferred AGRP/ASP fusion peptides of the present invention include fusions to an immunoglobulin constant region such as an Fc region. The human immunoglobulin hinge and Fc region can be fused at either the N-terminus or C-terminus of the AGRP/ASP peptides using methods known to the skilled artisan. The subsequent Fc-fusion peptide can be purified by use of a Protein A affinity column. Fc is known to exhibit a long pharmacokinetic half-life in vivo and peptides fused to Fc may thus exhibit a substantially greater half-life in vivo than the unfused counterpart. In addition, fusion to the Fc region allows for dimerization and/or multimerization of the fusion peptide.

AGRP/ASP peptide derivatives are included in the scope of the present invention. Such derivatives are chemically modified AGRP/ASP peptide compositions. Such modifications include, without limitation, acylating the amino terminus of the peptide and/or linking the peptide to a polymer.

Acetylation of the amino terminus ("N-terminus") of each AGRP/ASP peptide can be carried out with any of several alkyl carboxylic acids. "Alkyl carboxylic acids" refers to a straight or branched chain saturated aliphatic hydrocarbon-1 substitute of carboxylic acids where the number of carbons is preferably 1–10, including, without limitation, methyl, ethyl, n-propyl, isopropyl, n-butyl, isobutyl, tert-butyl, pentyl, isoamyl, n-hexyl, and the like. Acylation using alkyl carboxylic acids can be conducted using a number of activating reagents known in the art of peptide chemistry to affect the amide bond coupling between the carboxylate and the free amino group in the AGRP/ASP peptide. Such activating reagents include, without limitation, DCC (Dicyclohexyl carbodiimide), EDC (1-(3-dimethylaminopropyl)-3-ethylcarbodiimide), or DIC (diisopropylcarbodiimide) and can be used in the presence of a catalyst such as HOBT (N-hydroxybenzotriazole) HOAt (7-aza-N-hydroxybenzotriazole), HOSu, or DMAP (dimethylaminopyridine).

Where it is desirable to attach a polymer to the AGRP/ASP peptide, the polymer selected is typically water soluble so that the peptide to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of AGRP/ASP peptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the polymer acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1–C10 alkoxy or aryloxy derivatives thereof (see U.S. Pat. No. 5,252,714).

Pegylation of AGRP/ASP peptides may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated AGRP/ASP peptides will generally comprise the steps of (a) reacting the peptide with polyethylene glycol (such as a reactive ester or aldehyde derivative of PEG) under conditions whereby AGRP/ASP peptide becomes attached to one or more PEG groups, and (b) obtaining the reaction product(s). In general, the optimal reaction conditions for the acylation reactions will be determined based on known parameters and the desired result. For example, the larger the ratio of PEG: peptide, the greater the percentage of poly-pegylated product.

In a preferred embodiment, the AGRP/ASP peptide derivative will have a single PEG moiety at the N terminus.

Generally, conditions which may be alleviated or modulated by administration of the present AGRP/ASP peptide derivative include those described herein for AGRP/ASP peptides. However, the AGRP/ASP peptide derivative disclosed herein may have additional activities, enhanced or reduced biological activity, or other characteristics, such as increased or decreased half-life, as compared to the non-derivatized molecules.

AGRP/ASP Antibodies

AGRP/ASP peptide may be used as an immunogen to generate anti-AGRP/ASP peptide antibodies. Such antibodies, which specifically bind to AGRP/ASP peptide, are useful as standards in assays for AGRP/ASP peptide, such as by labeling purified AGRP/ASP peptide for use as a standard in a radioimmunoassay, enzyme-linked immunoassay, or competitive-type receptor binding assays radioreceptor assay, as well as in affinity purification techniques. Ordinarily, the anti-AGRP/ASP peptide antibody will bind AGRP/ASP peptide with an affinity of at least about $10^6$ L/mole, and preferably at least about $10^7$ L/mole, and preferably at least about $10^7$ L/mole.

Polyclonal antibodies directed toward AGRP/ASP peptide generally can be raised in animals by multiple subcutaneous or intraperitoneal injections of AGRP/ASP peptide and an adjuvant. It may be useful to conjugate AGRP/ASP peptide or a peptide fragment thereof to a carrier protein that is immunogenic in the species to be immunized, such as keyhole limpet heocyanin, serum, albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (conjugation through lysine residues), glutaraldehyde, succinic anhydride, $SOCl_2$, or $R^1N=C=NR$, where R $R^1$ are different alkyl groups.

Animals can be immunized with such AGRP/ASP peptide carrier protein conjugates combined 1 mg or 1 μg of conjugate (for rabbits or mice, respectively) with 3 volumes of Freund's complete adjuvant and injecting the solution intradermally at multiple sites. One month later the animals are boosted with $\frac{1}{5}^{th}$ to $\frac{1}{10}^{th}$ the original amount of conjugate in Freund's complete adjuvant by subcutaneous injection at multiple sites. Seven to 14 days later animals are bled and the serum is assayed for anti-AGRP/ASP peptide antibody titer. Animals are boosted until the antibody titer plateaus. Preferably, the animal is boosted by injection with a conjugate of the same AGRP/ASP peptide with a different carrier protein and/or through a different cross-linking agent. Conjugates of AGRP/ASP peptide and a suitable carrier protein also can be made in recombinant cell culture as fusion proteins. Also, aggregating agents such as alum are used to enhance the immune response.

Monoclonal antibodies directed toward AGRP/ASP peptide are produced using any method which provides for the production of antibody molecules by continuous cell lines in culture. The modifier "monoclonal" indicates the character of the antibody as being obtained from a substantially homogeneous population of antibodies, and is not to be construed as requiring production of the antibody by any particular method. Examples of suitable methods for preparing monoclonal antibodies include hybridoma method of Kohler, et al., Nature 256: 495–497 (1975), and the human B-cell hybridoma method, Kozbor, J. Immunol. 133: 3001 (1984); Brodeur, et al., Monoclonal Antibody Production Techniques and Applications, pp. 51–63 (Marcel Dekker, Inc., New York, 1987).

The monoclonal antibodies of the invention specifically include "chimeric" antibodies (immunoglobulines) in which a portion of the heavy and/or light chain is identical with or homologous to corresponding sequence in antibodies derived from a particular species or belonging to a particular antibody class or subclass, while the remainder of the chains(s) is identical with or homologous to corresponding sequence in antibodies derived from another species or belonging to another antibody class or subclass, as well as fragments of such antibodies, so long as they exhibit the desired biological activity (Cabilly, et al., U.S. Pat. No. 4,816,567; Morrison et al., Proc. Natl. Acad. Sci. USA, 81: 6851–6855 [1985]).

In a preferred embodiment, the chimeric anti-AGRP/ASP peptide antibody is a "humanized" antibody. Methods for humanizing non-human antibodies are well known in the art. Generally, a humanized antibody has one or more amino acid residues introduced into it from a source which is non-human. These non-human amino acids residues are often referred to as "import" residues, which are typically taken from an "import" variable domain.

Humanization can be performed following methods known in the art (Jones, et al., Nature 321: 522–525 (1986); Riechmann, et al., Nature, 332: 323–327 (1988); Verhoeyen, et al., Science 239: 1534–1536 (1988)), by substituting rodent complementarily-determining regions (CDRs) for the corresponding regions of a human antibody. Alternatively, it is now possible to produce transgenic animals (e.g., mice) that are capable, upon immunization, or producing a full repertoire of human antibodies in the absence of endogenous immunoglobulin production. For example, it has been described that the homozygous deletion of the antibody heavy-chain joining region ($J_H$) gene in chimeric and germ-line immunoglobulin gene array in such germ-line mutant mice will result in the production of human antibodies upon antigen challenge. See, for example, Jakobovits, et al., Proc. Natl. Acad. Sci. 90: 2551–2555 (1993); Jakobovits, et al., Nature 362: 255–258 (1993); Bruggermann, et al., Year in Immuno. 7:33 (1993). Human antibodies can also be produced in phage-display libraries (Hoogenboom, et al., J. Mol. Biol. 227:381 (1991); Marks, et al., J. Mol. Biol. 222:581 (1991).

For diagnostic applications, anti-AGRP/ASP peptide antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isotheocyanate, rhodamine, or luciferin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by David et al., Biochemistry 13: 1014–1021 (1974); Pain et al., J. Immunol. Meth. 40: 216–231 (1981); and Bayer et al., Meth. Enz. 184: 138–163 (1990).

The anti-AGRP/ASP peptide antibodies may be employed in any known assay method, such as competitive binding assays, direct and indirect sandwich assays, and immunoprecipitation assays (Sola, Monoclonal Antibodies: A Manual of Techniques, pp. 147–158, CRC Press, Inc., [1987]).

Competitive binding assays rely on the ability of a labeled standard (e.g., AGRP/ASP peptide or an immunologically reactive portion thereof) to compete with the test sample analyte (AGRP/ASP peptide) for binding with a limited amount of antibody. The amount of AGRP/ASP peptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex (see David et al., U.S. Pat. No. 4,376,110). The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

Neutralizing anti-AGRP/ASP peptide antibodies are useful as antagonists of AGRP/ASP peptide. The term "neutralizing anti-AGRP/ASP peptide antibody" as used herein refers to an antibody that is capable of specifically binding to AGRP/ASP peptide, and which is capable of substantially inhibiting or eliminating the functional activity of AGRP/ASP peptide in vivo or in vitro. Typically a neutralizing antibody will inhibit the functional activity of AGRP/ASP peptide at least about 50%, and preferably greater that 80%, as determined, for example, by an in vitro receptor binding assay.

Therapeutic Compositions and Administration

Therapeutic compositions of AGRP/ASP peptides are within the scope of the present invention. Such compositions may comprise a therapeutically effective amount of the peptide or fragments, variants, or derivatives in admixture with a pharmaceutically acceptable carrier. Optionally, the peptide may be formulated in a acid-salt form. The carrier material may be water for injection, preferably supplemented with other materials common in solutions for administration to mammals such as, for example, alumina, lecithin, d-alpha-tocopherol, polyethyleneglycol, surfactants, serum proteins such as human serum albumin, phosphates, glycine, sorbic acid, and potassium sorbate.

Typically, an AGRP/ASP peptide therapeutic compound will be administered in the form of a composition comprising purified peptide, fragment, variant, or derivative, optionally in its salt form, in conjunction with one or more physiologically acceptable carriers, excipients, or diluents.

Pharmaceutically acceptable salts of for the peptides of the present invention include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycolate, hemisulfate, hydrochloride, hydrobromide, hydroiodide, lactate, maleate, malonate, methanesulfonate, nicotinate, nitrate, oxalate, pectinate, phosphate, salicylate, succinate, sulfate, tartrate, thiocyanate, and other such pharmaceutically acceptable salts.

Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The AGRP/ASP peptide compositions can be administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of AGRP/ASP peptide compositions useful for practicing the present invention may be prepared for storage by mixing the selected composition having the desired degree of purity with optional physiologically acceptable carriers, excipients, or stabilizers (Remington's *Pharmaceutical Sciences,* 18th Edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the AGRP/ASP peptide composition(s) to be employed therapeutically will depend, for example, upon the therapeutic objectives such as the indication for which the AGRP/ASP peptide is being used, the route of administration, and the condition of the patient. Accordingly, it will be necessary for the therapist to titer the dosage and modify the route of administration as required to obtain the optimal therapeutic effect. A typical daily dosage may range from about 0.1 mg/kg to up to 100 mg/kg or more, depending on the factors mentioned above. Typically, a clinician will administer the composition until a dosage is reached that achieves the desired effect. The composition may therefore be administered as a single dose, or as two or more doses (which may or may not contain the same amount of AGRP/ASP peptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The AGRP/ASP peptide composition to be used for in vivo administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accordance with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Alternatively or additionally, the composition may be administered locally via implantation into the selected area using a membrane, sponge, or other appropriate material on to which AGRP/ASP peptide has been absorbed.

Where an implantation device is used, the device may be implanted into any suitable tissue or organ, and delivery of AGRP/ASP peptide may be directly through the device via bolus, or via continuous administration, or via catheter using continuous infusion.

AGRP/ASP peptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547–556 [1983]), poly (2-hydroxyethyl-methacrylate) (Langer et al., *J. Biomed. Mater. Res.,* 15: 167–277 [1981] and Langer, *Chem. Tech.,* 12: 98–105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., Eppstein et al., *Proc. Natl. Acad. Sci. USA,* 82: 3688–3692 [1985]; EP 36,676; EP 88,046; EP 143,949).

The AGRP/ASP peptides, fragments, variants, and derivatives thereof, may be employed alone, together, or in combination with other pharmaceutical compositions. The AGRP/ASP peptides, fragments, variants, and derivatives may be used in combination with cytokines, hormones, growth factors, antibiotics, anti-inflammatories, and/or chemotherapeutic agents as is appropriate for the indication being treated.

In some cases, it may be desirable to use AGRP/ASP peptide compositions in an ex vivo manner. Here, cells, tissues, or organs that have been removed from the patient are exposed to AGRP/ASP peptide compositions after which the cells, tissues and/or organs are subsequently implanted back into the patient.

In other cases, AGRP/ASP peptide may be delivered through implanting into patients certain cells that have been genetically engineered, using methods such as those described herein, to express and secrete the polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975 (Baetge et al., CytoTherapeutics, Inc.). The cells, with or without encapsulation, may be implanted into suitable body tissues or organs of the patient.

As discussed above, it may be desirable to treat isolated cell populations such as, for example, brain cells and/or neurons with one or more AGRP/ASP peptides, variants, derivatives and/or fragments. This can be accomplished by exposing the isolated cells to the AGRP/ASP peptide, variant, derivative, or fragment directly, where it is in a form that is permeable to the cell membrane.

Utility

The AGRP/ASP peptides of the present invention are expected to have utility as modulators of feeding behavior based on their amino acid sequence similarity to a portion of full length AGRP/ASP.

AGRP/ASP nucleic acid molecules and fragments thereof that do not themselves encode AGRP/ASP peptides that are active in activity assays may be useful as hybridization probes in diagnostic assays to test, either qualitatively or quantitatively, for the presence of AGRP/ASP DNA or corresponding RNA in mammalian tissue or bodily fluid samples.

AGRP/ASP peptide fragments, variants, and/or derivatives, whether biologically active or not, may be useful for preparing antibodies that recognize AGRP/ASP peptides.

The antibodies may be used therapeutically, such as to inhibit binding of the AGRP/ASP peptide to the melanocortin receptors, such as, for example, melanocortin-1 receptor and melanocortin-4 receptor. The antibodies may further be used for in vivo and in vitro diagnostic purposes, such as in labeled form to detect the presence of AGRP/ASP peptide in a body fluid or cell sample.

The following examples are intended for illustration purposes only, and should not be construed as limiting the scope of the invention in any way.

EXAMPLES

Example 1

AGRP/ASP Peptide Synthesis

All peptides were synthesized by the Fmoc (fluorenylmethoxycarbonyl)/t-butyl based solid phase peptide chemistry method using standard procedures known in the art. An ABI 431A peptide synthesizer (Perkin Elmer Corp., Foster City, Calif.) was used with a single coupling program to carry out the chain assembly. Commercially available preloaded Fmoc-AAA-HMP derivatized polystyrene resin (Midwest Biotech, Fishers, Ind. or Calbiochem, San Diego, Calif.) was used to prepare the C-terminal amino acid. Subsequent amino acids were coupled in 20 fold excess as HOBT (hydroxybenztriazole) esters using carbodiimide activation. The side-chain protecting groups for each amino acid were as follows: Arg(Pbf; 2,2,4,6,7-pentamethyldihydrobenzofuran-5-sulfonyl), Asn(Trt; trityl), Asp(OtBu; O-tert-butyl), Cys(Trt; trityl), Cys(Acm; aceteLmidomethyl), Gln(Trt; trityl), Glu(OtBu; O-tert-butyl), His(Trt; trityl), Lys(Boc; tert-butoxycarbonyl), Ser (tBu; tert-butyl), Thr(tBu), and Tyr(tBu; tert-butyl). Upon removal of the final N-terminal Fmoc with 20 percent piperidine in N-methylpyrrolidone, side-chain protecting groups were then removed and the peptide(s) were cleaved from the resin by treatment with TFA (trifluoroacetic acid): triisopropylsilane: water (92.5, 2.5, 5 v/v) for about 4 hours. The resulting suspension was filtered, and the filtrate volume reduced by roto-evaporation. The crude peptides were precipitated and washed with ether, followed by drying in-vacuo.

The linear (fully reduced) peptide intermediates were purified by HPLC prior to either an equilbrium oxidative refold or a two step oxidative cyclization process. The connectivity of those peptides containing one or two disulfides is unambiguous as a result of using orthogonal cysteine protection and oxidative-cyclization methods as follows. The first disulfide bond was formed using air oxidation (Cys[Trt]protection) and the second disulfide bond was formed by iodine treatment on the bis-Cys(Acm) containg mono-cyclic peptide intermediate. For the two peptides containing three disulfide bridges, oxidation was carried out using 10 percent DMSO (dimethylsulfoxide) oxidation under acidic conditions.

Each crude peptide was dissolved in 8M guanidine containing 100 mM DTT (dithiothreitol) and purified to at least 95 percent homogeneity by preparative reverse-phase HPLC using a Vydac $C_{18}$ (2.5 cm×25 cm) column (Vydac Corp., Hesperia, Calif.) with a linear gradient of 0.1 percent TFA (v/v) in water and 0.05 percent TFA (v/v) in acetonitrile.

The composition of each peptide was assessed using electro-spray ionization (ESI) mass spectromerty and amino acid analysis. Mass spectra for each synthetic peptide was obtained on a Sciex API (Perkin Elmer Corp., Foster City, Calif.) single quadropole mass spectrometer, and reported as m/z (M+1). All mass spectral samples were obtained as fractions off of the preparative HPLC purification.

Amino acid analyses of each peptide were performed on an ABI 420A hydrolyzer/derivatizer (ABI, Foster City, Calif.) using a 130A separation system (ABI, Foster City, Calif.). The peptides were hydrolyzed using 6N HCl at 200° for 30 minutes and then derivatized using the defined instrument protocol in the ABI AAA420A Operator's Manual as PTC (phenylisothiocynate) derivatives. The amino acid mixture was then separated by HPLC on a Brownlee PTC $C_{18}$ Collumn (ABI, Foster City, Calif.), 5 micron pore size, 2.1×220 mm, with a linear gradient of water and acetonitrile. Both solvents were buffered with sodium acetate to a pH of about 5.4. The amino acid composition of each peptide was then determined by comparison of the unknown peak ratios with an equimolar amino acid standard. Each peptide generated experimental data that conformed with expected theoretical values.

N-terminal acetylation of those peptides that were acetylated was carried out following removal of the final N-terminal protecting group by treatment of the resin-bound side chain protected peptide with 20 percent acetic anhydride in N-methyl pyrrolidone using standard procedures.

The synthesized peptides include the following (from amino to carboxy terminus):
SEQ ID NO:1:
Met-Arg-Cys-Val-Arg-Leu-His-Glu-Ser-Cys-Leu-Gly-Gln-Gln-Val-Pro-Cys-Cys-Asp-Pro-Cys-Ala-Thr-Cys-Tyr-Cys-Arg-Phe-Phe-Asn-Ala-Phe-Cys-Tyr-Cys-Arg-Lys-Leu-Gly-Thr-Ala-Met-Asn-Pro-Cys-Ser-Arg-Thr
SEQ ID NO:1 is native human AGRP from amino acids 65–112.
SEQ ID NO:2:
His-Glu-Ser-Cys-Leu-Gly-Gln-Gln-Val-Pro-Cys-Abu-Asp-Pro-Abu-Ala-Thr-Cys-Tyr-Cys-Arg-Phe-Phe-Asn-Ala-Phe-Cys-Tyr-Cys-Arg-Lys-Leu
SEQ ID NO):2 is amino acids 71–103 of human AGRP/ASP with amino acids 82 and 85 of native AGRP replaced by amino butyric acid (Abu).
SEQ ID NO:3:
His-Glu-Ser-Cys-Leu-Gly-Gln-Gln-Val-Pro-Abu-Abu-Asp-Pro-Abu-Ala-Thr-Cys-Tyr-Cys-Arg-Phe-Phe-Asn-Ala-Phe-Cys-Tyr-Abu-Arg-Lys-Leu
SEQ ID NO:3 is amino acids 71–103 of human AGRP with amino acids 81, 82, 85, and 99 of native AGRP replaced by amino butyric acid (Abu).
SEQ ID NO:4:
His-Glu-Ser-Abu-Leu-Gly-Gln-Gln-Val-Pro-Cys-Abu-Asp-Pro-Abu-Ala-Thr-Abu-Tyr-Cys-Arg-Phe-Phe-Asn-Ala-Phe-Cys-Tyr-Cys-Arg-Lys-Leu
SEQ ID NO:4 is amino acids 71–103 of human AGRP with amino acids 74, 82, 85, and 88 of native AGRP replaced by amino butyric acid (Abu).

SEQ ID NO:5:
His-Glu-Ser-Cys-Leu-Gly-Gln-Gln-Val-Pro-Cys-Abu-Asp-Pro-Abu-Ala-Thr-Cys-Tyr-Abu-Arg-Phe-Phe-Asn-Ala-Phe-Abu-Tyr-Cys-Arg-Lys-Leu
SEQ ID NO:5 is amino acids 71–103 of human AGRP with amino acids 82, 85, 90 and 97 of native AGRP replaced by amino butyric acid (Abu).
SEQ ID NO:6:
Cys-Arg-Phe-Phe-Asn-Ala-Phe-Cys
SEQ ID NO:6 is amino acids 90–97 of human AGRP.
SEQ ID NO:7:
Cys-Arg-Phe-Phe-Gly-Ser-Ala-Cys
SEQ ID NO:7 is amino acids 115–122 of native human ASP.
SEQ ID NO:8:
Cys-Abu-Asp-Pro-Cys-Ala-Thr-Abu-Tyr-Cys-Arg-Phe-Phe-Asn-Ala-Phe-Cys-Tyr-Cys-Arg-Lys-Leu-Gly-Thr-Ala-Met-Asn-Pro-Cys-Ser-Arg-Thr
SEQ ID NO:8 is amino acids 81–112 of human AGRP with amino acids 82 and 88 of native AGRP replaced by amino butyric acid (Abu).
SEQ ID NO:9:
Abu-Abu-Asp-Pro-Cys-Ala-Thr-Abu-Tyr-Cys-Arg-Phe-Phe-Asn-Ala-Phe-Cys-Tyr-Abu-Arg-Lys-Leu-Gly-Thr-Ala-Met-Asn-Pro-Cys-Ser-Arg-Thr
SEQ ID NO:9 is amino acids 81–112 of human AGRP with amino acids 81, 82, 88, and 90 of native AGRP replaced by amino butyric acid (Abu).
SEQ ID NO:10:
Cys-Abu-Asp-Pro-Abu-Ala-Thr-Abu-Tyr-Cys-Arg-Phe-Phe-Asn-Ala-Phe-Cys-Tyr-Cys-Arg-Lys-Leu-Gly-Thr-Ala-Met-Asn-Pro-Abu-Ser-Arg-Thr
SEQ ID NO:10 is amino acids 81–112 of human AGRP/ with amino acids 82, 85, 88, and 109 of native AGRP replaced by amino butyric acid (Abu).
SEQ ID NO:11:
Cys-Abu-Asp-Pro-Cys-Ala-Thr-Abu-Tyr-Abu-Arg-Phe-Phe-Asn-Ala-Phe-Abu-Tyr-Cys-Arg-Lys-Leu-Gly-Thr-Ala-Met-Asn-Pro-Cys-Ser-Arg-Thr
SEQ ID NO:11 is amino acids 81–112 of human AGRP with amino acids 82, 88, 90, and 97 of native AGRP replaced by amino butyric acid (Abu).
SEQ ID NO:12:
Cys-Abu-Asp-Pro-Abu-Ala-Thr-Abu-Tyr-Cys-Arg-Phe-Phe-Asn-Ala-Phe-Cys-Tyr-Cys-Arg-Lys-Leu
SEQ ID NO:12 is amino acids 81–103 of human AGRP with amino acids 82, 85, and 88 of native AGRP replaced by amino butyric acid (Abu).
SEQ ID NO:13:
Arg-Asn-Ser-Cys-Lys-Pro-Pro-Ala-Pro-Ala-Cys-Abu-Asp-Pro-Abu-Ala-Ser-Cys-Gln-Cys-Arg-Phe-Phe-Arg-Ser-Ala-Cys-Ser-Cys-Arg-Val-Leu SEQ ID NO:13 is amino acids 96–127 of human ASP with amino acids 107 and 110 of native ASP replaced by amino butyric acid (Abu).
SEQ ID NO:14:
Arg-Asn-Ser-Cys-Lys-Pro-Pro-Ala-Pro-Ala-Abu-Abu-Asp-Pro-Abu-Ala-Ser-Cys-Gln-Cys-Arg-Phe-Phe-Arg-Ser-Ala-Cys-Ser-Abu-Arg-Val-Leu
SEQ ID NO:14 is amino acids 96–127 of human ASP with amino acids 106, 107, 110 and 124 of native ASP replaced by amino butyric acid (Abu).
SEQ ID NO:15:
Arg-Asn-Ser-Abu-Lys-Pro-Pro-Ala-Pro-Ala-Cys-Abu-Asp-Pro-Abu-Ala-Ser-Abu-Gln-Cys-Arg-Phe-Phe-Arg-Ser-Ala-Cys-Ser-Cys-Arg-Val-Leu
SEQ ID NO:15 is amino acids 96–127 of human ASP with amino acids 100, 107, 110 and 113 of native ASP replaced by amino butyric acid (Abu).

SEQ ID NO:16:
Ala-Cys-Abu-Asp-Pro-Abu-Ala-Ser-Abu-Gln-Cys-Arg-
 Phe-Phe-Arg-Ser-Ala-Cys-Ser-Cys-Arg-Val-Leu
 SEQ ID NO:16 is amino acids 105–127 of human ASP
with amino acids 107, 110, and 113 of native ASP replaced
by amino butyric acid (Abu).
SEQ ID NO:17:
Abu-Abu-Asp-Pro-Cys-Ala-Ser-Abu-Gln-Cys-Arg-Phe-
 Phe-Arg-Ser-Ala-Cys-Ser-Abu-Arg-Val-Leu-Ser-Leu-
 Asn-Cys
 SEQ ID NO:17 is amino acids 106–131 of human ASP
with amino acids 106, 107, 113, and 124 of native ASP
replaced by amino butyric acid (Abu).
SEQ ID NO:18:
Cys-Abu-Asp-Pro-Cys-Ala-Ser-Abu-Gln-Abu-Arg-Phe-
 Phe-Arg-Ser-Ala-Abu-Ser-Cys-Arg-Val-Leu-Ser-Leu-
 Asn-Cys
 SEQ ID NO:18 is amino acids 106–131 of human ASP
with amino acids 107, 113, 115, and 122 of native ASP
replaced by amino butyric acid (Abu).
SEQ ID NO:19:
Cys-Ala-Asp-Pro-Ala-Ala-Thr-Ala-Tyr-Cys-Arg-Phe-Phe-
 Asn-Ala-Phe-Cys-Tyr-Cys-Arg-Lys-Leu
 SEQ ID NO:19 is amino acids 81–103 of native human
AGRP with amino acids 82, 85, and 88 replaced by alanine
(Ala).
SEQ ID NO:20:
Cys-Ala-Ala-Pro-Ala-Ala-Thr-Ala-Tyr-Cys-Arg-Phe-Phe-
 Asn-Ala-Phe-Cys-Tyr-Cys-Arg-Lys-Leu
 SEQ ID NO:20 is amino acids 81–103 of native human
AGRP with amino acids 82, 83, 85, and 88 replaced by
alanine (Ala).
SEQ ID NO:21:
Cys-Ala-Asp-Pro-Ala-Ala-Thr-Ala-Tyr-Cys-Ala-Phe-Phe-
 Asn-Ala-Phe-Cys-Tyr-Cys-Arg-Lys-Leu
 SEQ ID NO:21 is amino acids 81–103 of native human
AGRP with amino acids 82, 83, 88, and 91 replaced by
alanine (Ala).
SEQ ID NO:22:
Cys-Ala-Asp-Pro-Ala-Ala-Thr-Ala-Tyr-Cys-Arg-Ala-Phe-
 Asn-Ala-Phe-Cys-Tyr-Cys-Arg-Lys-Leu
 SEQ ID NO:22 is amino acids 81–103 of native human
AGRP with amino acids 82, 85, 88, and 92 replaced by
alanine (Ala).
SEQ ID NO:23:
Cys-Ala-Asp-Pro-Ala-Ala-Thr-Ala-Tyr-Cys-Arg-Phe-Ala-
 Asn-Ala-Phe-Cys-Tyr-Cys-Arg-Lys-Leu
 SEQ ID NO:23 is amino acids 81–103 of native human
AGRP with amino acids 82, 85, 88, and 93 replaced by
alanine (Ala).
SEQ ID NO:24:
Ac-Asp-Pro-Ala-Ala-Thr-Ala-Tyr-Cys-Arg-Phe-Phe-Asn-
 Ala-Phe-Cys-Tyr-Ala-Arg-Lys-Leu
 SEQ ID NO:24 is amino acids 83–102 of native human
AGRP with amino acids 85, 88 and 100 replaced by alanine
(Ala), and in which the amino terminus is acetylated.
SEQ ID NO:25:
Ala-Cys-Ala-Ala-Pro-Ala-Ala-Ser-Ala-Gln-Cys-Arg-Phe-
 Phe-Arg-Ser-Ala-Cys-Ser-Cys-Arg-Val-Leu
 SEQ ID NO:25 is amino acids 105–127 of human ASP in
which amino acids 107, 108, 110, and 113 of native ASP are
replaced by alanine (Ala).
SEQ ID NO:26:
Ac-Asp-Pro-Ala-Ala-Ser-Ala-Gln-Cys-Arg-Phe-Phe-Arg-
 Ser-Ala-Cys-Ser-Ala-Arg-Val-Leu
 SEQ ID NO:26 is amino acids 108–127 of human ASP in
which amino acids 110, 113, and 124 of native ASP are
replaced by alanine (Ala) and the amino terminus is acety-
lated (Ac).

The DNA molecules corresponding to each of the above
peptides is set forth below. Where the peptide contains the
non-naturally occurring amino acid Abu (amino butyric
acid), the codon for alanine (Ala) has been substituted for
Abu. All sequences are listed in the 5' to 3' direction.
In these sequences, A, T, C, and G have their usual
meanings; "M" can be A or C; "N" can be A, T, C, or G; "R"
can be A or G; "W" can be A or T; and "Y" can be C or T.
SEQ ID NO:27 (corresponding to the peptide of SEQ ID
 NO:1):
ATGMGNTGYGTNMGNYTNCAYGARWSNT-
 GYYTNGGNCARCARGTNCCNTGYTGYG AYC-
 CNTGYGCNACNTGYTAYTGYMGNTTYT-
 TYAAYGCNTTYTGYTAYTGYMGNAA
 RYTNGGNACNGCNATGAAYCCNTGYWSN-
 MGNACN
SEQ ID NO:28 (corresponding to the peptide of SEQ ID
 NO:2):
CAYGARWSNTGYYTNGGNCARCARGTNC-
 CNGCNGCNGAYCCNGCNGCNACNTGYT AYT-
 GYMGNTTYTTYAAYGCNTTYTGYTAYGC-
 NMGNAARYTN
SEQ ID NO:29 (corresponding to the peptide of SEQ ID
 NO:3):
CAYGARWSNTGYYTNGGNCARCARGTNC-
 CNGCNGCNGAYCCNGCNGCNACNTGYT AYT-
 GYMGNTTYTTYAAYGCNTTYTGYTAYGC-
 NMGNAARYTN
SEQ ID NO:30 (corresponding to the peptide of SEQ ID
 NO:4):
CAYGARWSNGCNYTNGGNCARCARGTNC-
 CNTGYGCNGAYCCNGCNGCNACNGCNT AYT-
 GYMGNTTYTTYAAYGCNTTYTGYTAYT-
 GYMGNAARYTN
SEQ ID NO:31 (corresponding to the peptide of SEQ ID
 NO:5):
CAYGARWSNTGYYTNGGNCARCARGTNC-
 CNTGYGCNGAYCCNGCNGCNACNTGYT AYGCN-
 MGNTTYTTYAAYGCNTTYGCNTAYTGYM-
 GNAARYTN
SEQ ID NO:32 (corresponding to the peptide of SEQ ID
 NO:6):
TGYMGNTTYTTYAAYGCNTTYTGY
SEQ ID NO:33 (corresponding to the peptide of SEQ ID
 NO:7):
TGYMGNTTYTTYGGNWSNGCNTGY
SEQ ID NO:34 (corresponding to the peptide of SEQ ID
 NO:8):
TGYGCNGAYCCNTGYGCNACNGCNTAYT-
 GYMGNTTYTTYAAYGCNTTYTGYTAYT GYMG-
 NAARYTNGGNACNGCNATGAAYCCNTGY-
 WSNMGNACN
SEQ ID NO:35 (corresponding to the peptide of SEQ ID
 NO:9):
GCNGCNGAYCCNTGYGCNACNGCNTAYT-
 GYMGNTTYTTYAAYGCNTTYTGYTAYG CNMG-
 NAARYTNGGNACNGCNATGAAYCCNTGY-
 WSNMGNACN
SEQ ID NO:36 (corresponding to the peptide of SEQ ID
 NO:10):
TGYGCNGAYCCNGCNGCNACNGCNTAYT-
 GYMGNTTYTTYAAYGCNTTYTGYTAYT GYMG-
 NAARYTNGGNACNGCNATGAAYCCNGCN-
 WSNMGNACN
SEQ ID NO:37 (corresponding to the peptide of SEQ ID
 NO:11):
TGYGCNGAYCCNTGYGCNACNGCN-
 TAYGCNMGNTTYTTYAAYGCNTTYGCNTAYT

GYMGNAARYTNGGNACNGCNATGAAYC-
CNTGYWSNMGNACN

SEQ ID NO:38 (corresponding to the peptide of SEQ ID NO:12):
TGYGCNGAYCCNGCNGCNACNGCNTAYT-
GYMGNTTYTTYAAYGCNTTYTGYTAYT GYMG-
NAARYTN SEQ ID NO:39 (corresponding to the peptide of SEQ ID NO:13):
MGNAAYWSNTGYAARCCNCCNGCNC-
CNGCNTGYGCNGAYCCNGCNGCNWSNTGYC
ARTGYMGNTTYTTYMGNWSNGCNTGY-
WSNTGYMGNGTNYTN SEQ ID NO:40 (corresponding to the peptide of SEQ ID NO:14):
MGNAAYWSNTGYAARCCNCCNGCNC-
CNGCNGCNGAYCCNGCNGCNWSNTGYCART
GYMGNTTYTTYMGNWSNGCNTGYWSNGC-
NMGNGTNYTN SEQ ID NO:41 (corresponding to the peptide of SEQ ID NO:15):
MGNAAYWSNGCNAARCCNCCNGCNC-
CNGCNTGYGCNGAYCCNGCNWSNGCNWSNG
CNCARTGYMGNTTYTTYMGNWSNGCNT-
GYWSNTGYMGNGTNYTN SEQ ID NO:42 (corresponding to the peptide of SEQ ID NO:16):
GCNTGYGCNGAYCCNGCNGCNWSNGCN-
CARTGYMGNTTYTTYMGNWSNGCNTGYW SNT-
GYMGNGTNYTN SEQ ID NO:43 (corresponding to the peptide of SEQ ID NO:17):
GCNGCNGAYCCNTGYGCNWSNGCNCART-
GYMGNTTYTTYMGNWSNGCNTGYWSNG
CNMGNGTNYTNWSNYTNAAYTGY SEQ ID NO:44 (corresponding to the peptide of SEQ ID NO:18):
TGYGCNGAYCCNTGYGCNWSNGCN-
CARGCNMGNTTYTTYMGNWSNGCNGCNWSNT
GYMGNGTNYTNWSNYTNAAYTGY SEQ ID NO:45 (corresponding to the peptide of SEQ ID NO:19):
TGYGCNGAYCCNGCNGCNACNGCNTAYT-
GYMGNTTYTTYAAYGCNTTYTGYTAYT GYMG-
NAARYTN SEQ ID NO:46 (corresponding to the peptide of SEQ ID NO:20):
TGYGCNGCNCCNGCNGCNACNGCNTAYT-
GYMGNTTYTTYAAYGCNTTYTGYTAYT GYMG-
NAARYTN SEQ ID NO:47 (corresponding to the peptide of SEQ ID NO:21):
TGYGCNGAYCCNGCNGCNACNGCNTAYT-
GYGCNTTYTTYAAYGCNTTYTGYTAYT GYMG-
NAARYTN SEQ ID NO:48 (corresponding to the peptide of SEQ ID NO:22):
TGYGCNGAYCCNGCNGCNACNGCNTAYT-
GYMGNGCNTTYAAYGCNTTYTGYTAYT GYMG-
NAARYTN SEQ ID NO:49 (corresponding to the peptide of SEQ ID NO:23):
TGYGCNGAYCCNGCNGCNACNGCNTAYT-
GYMGNTTYGCNAAYGCNTTYTGYTAYT GYMG-
NAARYTN SEQ ID NO:50 (corresponding to the peptide of SEQ ID NO:24):
TGYGCNGAYCCNGCNGCNACNGCNTAYT-
GYMGNTTYTTYAAYGCNTTYTGYTAYG CNMG-
NAARYTN SEQ ID NO:51 (corresponding to the peptide of SEQ ID NO:25):
GCNTGYGCNGCNCCNGCNGCNWSNGCN-
CARTGYMGNTTYTTYMGNWSNGCNTGYW SNT-
GYMGNGTNYTN SEQ ID NO:52 (corresponding to the peptide of SEQ ID NO:26):
GAYCCNGCNGCNWSNGCNCARTGYMGNT-
TYTTYMGNWSNGCNTGYGCNGTNYTN These nucleic acid molecules can be prepared using methods described above in the Detailed Description.

Example 2

Melanocortin Receptor Binding Assays

Human embryonic kidney (HEK) 293 cells stably expressing human melanocortin-3 (MC-3) or human melanocortin-4 (MC-4) receptors were used for $^{125}$I-[Nle4, dPhe7]α-melanocte stimulating hormone (NDP-α-MSH) and $^{125}$I-AGRP radioligand binding studies.

For $^{125}$I-NDP-α-MSH binding, cells were collected in phosphate buffered saline (PBS) and homogenized in Buffer A containing about 25 mM HEPES and about 0.32 M sucrose (pH 7.4), after which the homogenate was spun at 48,000×g for 12 minutes. The resulting pellet, which contained the cell membrane fraction, was resuspended in Buffer B containing about 25 mM HEPES, Modified Eagle's medium (without phenol red), about 0.1 percent bovine serum albumin (BSA), about 0.1 mg/ml soybean trypsin inhibitor (STI) and about 0.1 mg/ml 4-(2-aminoethyl)-benzenesulfonyl fluoride (AEBSF) (pH 7.4), and spun at 48,000×g for 12 minutes. This step was repeated one additional time, and the final pellet was resuspended in Buffer B to a concentration of about 4 mg wet weight of cell membrane per ml.

The binding reaction was initiated by the addition of cell membrane extract (about 50 μl) to wells containing about 0.15 nM $^{125}$I-NDP-α-MSH (2000 Ci/mmole, Amersham, Arlington Heights, Ill.) and varying concentrations of unlabeled AGRP/ASP peptides. The final assay volume was 100 μl. The reaction mixture was incubated for about 180 minutes at 25 C. and the reaction was terminated by filtration over Unifilter 96 glass fiber filter plates that had been pre-soaked in 0.1 percent polyethylenimine (PEI). Filters were rinsed with ice-cold water, followed by the addition of about 37 μl of Packard MicroScint to each filter well. Radioactivity was quantified using a Packard TopCount. Each concentration of unlabeled AGRP/ASP peptide was tested in triplicate.

$^{125}$I-AGRP binding was performed identically to $^{125}$I-NDP-α-MSH binding with the exception that Buffer B contained 1 mM $MgCl_2$ and no MEM, and the final radioligand concentration was 1.10 nM. For $^{125}$I-AGRP binding, filters were rinsed with 0.5 M NaCl.

The results of the binding assays are shown in Table II below.

TABLE II

| Compound | hMC4 IC50 (nM) 125I NDP-MSH | hMC3 IC50 (nM) 125I-AGRP | hMC3 IC50 (nM) 125I NDP-MSH | hMC3 IC50 (nM) 125I-AGRP |
|---|---|---|---|---|
| HP228 | 27, 26 | 150, 104 | 117 | N/A |
| MTII | 6, 1 | 19, 14 | 20 | N/A |

TABLE II-continued

| Compound | hMC4 IC50 (nM) 125I NDP-MSH | hMC3 IC50 (nM) 125I-AGRP | hMC3 IC50 (nM) 125I NDP-MSH | hMC3 IC50 (nM) 125I-AGRP |
|---|---|---|---|---|
| alpha-MSH | 300, 200 | 733, >1000 | 255 | N/A |
| NDP-alpha-MSH | 8, 8, 4 | 4, 4 | 0.9, 0.7 | N/A |
| Mkd5-AGRP | 57, 65, 49 | 6, 7, 1 | 20, 10 | 0.7 |
| Md65-AGRP | 19 | N/A | 2 | N/A |
| SEQ ID NO:2 | 200 | 50 | >1000 | 850 |
| SEQ ID NO:3 | 900 | 160 | >1000 | >1000 |
| SEQ ID NO:4 | 100 | 13 | 850 | 90 |
| SEQ ID NO:5 | >1000 | 377 | >1000 | >1000 |
| SEQ ID NO:6 | >1000 | 636 | >1000 | >1000 |
| SEQ ID NO:7 | >1000 | 497 | >1000 | >1000 |
| SEQ ID NO:8 | >1000 | 300 | >1000 | >1000 |
| SEQ ID NO:8 | 900 | 200 | >1000 | 400 |
| SEQ ID NO:8 | 300 | 94 | 900 | 400 |
| SEQ ID NO:8 | 450 | 73 | 850 | 600 |
| SEQ ID NO:8 | 600 | 78 | >1000 | 800 |
| SEQ ID NO:9 | 600 | 73 | >1000 | 700 |
| SEQ ID NO:10 | 102 | 15 | 500 | 147 |
| SEQ ID NO:11 | >1000 | 800 | >1000 | >1000 |
| SEQ ID NO:12 | 114 | 13 | 650 | 101 |
| SEQ ID NO:13 | 1000 | 60 | >1000 | >1000 |
| SEQ ID NO:14 | >1000 | 900 | >1000 | >1000 |
| SEQ ID NO:15 | 800 | 45 | >1000 | >1000 |
| SEQ ID NO:16 | >1000 | 280 | >1000 | >1000 |
| SEQ ID NO:17 | >1000 | >1000 | >1000 | >1000 |
| SEQ ID NO:18 | >1000 | >1000 | >1000 | >1000 |

In this Table II, "N/A" refers to data not available. Six control compounds were used as a basis for comparison, and are listed in Table II as HP228, MTII, alpha-MSH, NDP-alpha MSH, Mkd5-AGRP, and Md65-AGRP. HP228 is a peptide having the sequence Ac-Nle-Gln-His-dPhe-Arg-dTrp-Gly (SEQ ID NO:53) where Ac is acetyl, Nle is norleucine and Dphe and dTrp are the D configurations of the respective amino acids; MTII is a peptide with the sequence Ac-Nle-Asp-His-dPhe-Arg-Trp-Lys (SEQ ID NO:54). Alpha-MSH is a natural ligand for both the MC-3 and the MC-4 receptors; NDP-alpha-MSH is a peptide having the sequence Ac-Nle-His-dPhe-Arg-Trp-Lys (SEQ ID NO:55), Mdk5-AGRP is full length human AGRP minus the first five amino terminal amino acid, and Md65-AGRP is the carboxy terminal fragment of AGRP spanning amino acids 65–112.

In some cases, assays were conducted in duplicate or triplicate, and the results are thus presented to indicate this (i.e., where there is more than one number for a given assay).

There are five sets of data for SEQ ID NO:8 due to the fact that this peptide contains 6 cys residues, and, when folded, the cys residues folded in five ways. Results are thus presented for each conformation. on-going research is being conducted to determine which molecule has which conformation. Two other peptides, SEQ ID NOs: 2 and 13, also have 6 cys residues, but when folded, each generated a single conformation (cys2–cys6; cys3–cys9; and cys 7–cys8).

SEQ ID NOs: 19–26 are "Ala scans" of AGRP 81–103, AGRP 83–103, ASP 105–127, and ASP 108–127 in which selected residues believed to be critical to MC-3 and MC-4 receptor binding have been substituted to alanine. While data is not presented for these molecules, it is believed that their binding affinity would be less than for the corresponding "native sequence" molecules.

Example 3

Cell Signaling Assay

The cell-based activity of the AGRP/ASP peptides can be tested by measuring the ability of each peptide to inhibit alpha-MSH stimulated cyclic AMP production in CHO K1 (or comparable mammalian cells) which stably express either the MC3 or MC4 receptor. The cells are also transfected with a reporter construct consisting of a cyclic AMP response element coupled to a reporter gene such as luciferase. Cyclic AMP production can then be indirectly quantified by measuring the activity of luciferase (or other reporter gene).

For example, cells can be plated at a density of about 4–5×10$^5$ cells/well in 96-well culture plates and the plates maintained at 37° C. in a humidified environment of 95 percent oxygen and 5 percent carbon dioxide in Ham's F12 media containing 10 percent FBS and PSG, and G418 at about 500 micrograms/milliter. On day 2, the media can be removed and replaced with serum-free media, and on day 3, the serum-free media can be removed and replaced with incubation buffer consisting of Ham's F12 media, 0.1 mM isobutylmethylxanthine, 0.1 percent BSA, and PSG. Experiments for determining dose responses to alpha-MSH can be performed in the presence of a fixed concentration of Mkd65-AGRP. Test compounds can be added to triplicate wells, and plates can be returned to the incubator for a period of about 8 hours after which the media can be removed and replaced with about 100 microliters of PBS. The PBS can subsequently be removed, and 100 microliters of lysis buffer (Promega, Madison, Wis.) can added to each well. Luciferase activity, defined as relative luciferase units (RLU), can be detected using a Promega assay kit and quantified using a Titertek Luminoscan (ICN Pharmaceuticals). The concentration of alpha-MSH producing 50 percent of the maximal stimulation of luciferase activity (ED50) can be determined using standard nonlinear regression analysis.

SEQUENCE LISTING

<160> NUMBER OF SEQ ID NOS: 55

<210> SEQ ID NO 1
<211> LENGTH: 48
<212> TYPE: PRT
<213> ORGANISM: Human

<400> SEQUENCE: 1

Met Arg Cys Val Arg Leu His Glu Ser Cys Leu Gly Gln Gln Val Pro
 1               5                  10                  15

```
Cys Cys Asp Pro Cys Ala Thr Cys Tyr Cys Arg Phe Phe Asn Ala Phe
            20                  25                  30

Cys Tyr Cys Arg Lys Leu Gly Thr Ala Met Asn Pro Cys Ser Arg Thr
        35                  40                  45

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid) at
      positions 12 and 15 and labeled as Xaa.

<400> SEQUENCE: 2

His Glu Ser Cys Leu Gly Gln Gln Val Pro Cys Xaa Asp Pro Xaa Ala
 1               5                  10                  15

Thr Cys Tyr Cys Arg Phe Phe Asn Ala Phe Cys Tyr Cys Arg Lys Leu
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid) at
      positions 11, 12, 15, and 29 and labeled as Xaa.

<400> SEQUENCE: 3

His Glu Ser Cys Leu Gly Gln Gln Val Pro Xaa Xaa Asp Pro Xaa Ala
 1               5                  10                  15

Thr Cys Tyr Cys Arg Phe Phe Asn Ala Phe Cys Tyr Xaa Arg Lys Leu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence:  AGRP
      Peptide Analog with synthetic amino acid (amino butyric acid) at
      positions 4, 12, 15 and 18 and labeled as Xaa.

<400> SEQUENCE: 4

His Glu Ser Xaa Leu Gly Gln Gln Val Pro Cys Xaa Asp Pro Xaa Ala
 1               5                  10                  15

Thr Xaa Tyr Cys Arg Phe Phe Asn Ala Phe Cys Tyr Cys Arg Lys Leu
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid) at
      positions 12, 15, 20 and 27 and labeled as Xaa.

<400> SEQUENCE: 5

His Glu Ser Cys Leu Gly Gln Gln Val Pro Cys Xaa Asp Pro Xaa Ala
 1               5                  10                  15

Thr Cys Tyr Xaa Arg Phe Phe Asn Ala Phe Xaa Tyr Cys Arg Lys Leu
            20                  25                  30
```

```
<210> SEQ ID NO 6
<211> LENGTH: 8
<212> TYPE: PRT
<213> ORGANISM: Human

<400> SEQUENCE: 6

Cys Arg Phe Phe Asn Ala Phe Cys
 1               5

<210> SEQ ID NO 7
<211> LENGTH: 8
<212> TYPE: PRT
<213> ORGANISM: Human

<400> SEQUENCE: 7

Cys Arg Phe Phe Gly Ser Ala Cys
 1               5

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid) at
      positions 2 and 8 and labeled as Xaa.

<400> SEQUENCE: 8

Cys Xaa Asp Pro Cys Ala Thr Xaa Tyr Cys Arg Phe Phe Asn Ala Phe
 1               5                  10                  15

Cys Tyr Cys Arg Lys Leu Gly Thr Ala Met Asn Pro Cys Ser Arg Thr
                20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid) at
      positions 1, 2, 8 and 19 and labeled as Xaa.

<400> SEQUENCE: 9

Xaa Xaa Asp Pro Cys Ala Thr Xaa Tyr Cys Arg Phe Phe Asn Ala Phe
 1               5                  10                  15

Cys Tyr Xaa Arg Lys Leu Gly Thr Ala Met Asn Pro Cys Ser Arg Thr
                20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid)
      located at positions 2, 5, 8 and 29 and labeled as Xaa.

<400> SEQUENCE: 10

Asp Xaa Pro Cys Xaa Ala Thr Xaa Tyr Cys Arg Phe Phe Asn Ala Phe
 1               5                  10                  15

Cys Tyr Arg Lys Leu Gly Thr Ala Met Asn Pro Cys Xaa Ser Arg Thr
                20                  25                  30

<210> SEQ ID NO 11
<211> LENGTH: 32
```

```
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid)
      located at positions 2, 8, 10 and 17 and labeled as Xaa.

<400> SEQUENCE: 11

Cys Xaa Asp Pro Cys Ala Thr Xaa Tyr Xaa Arg Phe Phe Asn Ala Phe
 1               5                  10                  15

Xaa Tyr Cys Arg Lys Leu Gly Thr Ala Met Asn Pro Cys Ser Arg Thr
             20                  25                  30

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: AGRP
      Peptide Analog with synthetic amino acid (amino butyric acid)
      located at positions 2, 5, and 8 and labeled as Xaa.

<400> SEQUENCE: 12

Cys Xaa Asp Pro Xaa Ala Thr Xaa Tyr Cys Arg Phe Phe Asn Ala Phe
 1               5                  10                  15

Cys Tyr Cys Arg Lys Leu
             20

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 12 and 15 and labeled as Xaa.

<400> SEQUENCE: 13

Arg Asn Ser Cys Lys Pro Pro Ala Pro Ala Cys Xaa Asp Pro Xaa Ala
 1               5                  10                  15

Ser Cys Gln Cys Arg Phe Phe Arg Ser Ala Cys Ser Cys Arg Val Leu
             20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 11, 12, 15 and 29 and labeled as Xaa.

<400> SEQUENCE: 14

Arg Asn Ser Cys Lys Pro Pro Ala Pro Ala Xaa Xaa Asp Pro Xaa Ala
 1               5                  10                  15

Ser Cys Gln Cys Arg Phe Phe Arg Ser Ala Cys Ser Xaa Arg Val Leu
             20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 4, 12, 15, and 18 and labeled as Xaa.
```

```
<400> SEQUENCE: 15

Arg Asn Ser Xaa Lys Pro Pro Ala Pro Ala Cys Xaa Asp Pro Xaa Ala
 1               5                  10                  15

Ser Xaa Gln Cys Arg Phe Phe Arg Ser Ala Cys Ser Cys Arg Val Leu
            20                  25                  30

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 3, 6 and 9 and labeled as Xaa.

<400> SEQUENCE: 16

Ala Cys Xaa Asp Pro Xaa Ala Ser Xaa Gln Cys Arg Phe Phe Arg Ser
 1               5                  10                  15

Ala Cys Ser Cys Arg Val Leu
            20

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 1, 2, 8 and 19 and labeled as Xaa.

<400> SEQUENCE: 17

Xaa Xaa Asp Pro Cys Ala Ser Xaa Gln Cys Arg Phe Phe Arg Ser Ala
 1               5                  10                  15

Cys Ser Xaa Arg Val Leu Ser Leu Asn Cys
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: ASP Peptide
      Analog with synthetic amino acid (amino butyric acid) located at
      positions 2, 8, 10 and 17 and labeled as Xaa.

<400> SEQUENCE: 18

Cys Xaa Asp Pro Cys Ala Ser Xaa Gln Xaa Arg Phe Phe Arg Ser Ala
 1               5                  10                  15

Xaa Ser Cys Arg Val Leu Ser Leu Asn Cys
            20                  25

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: AGRP
      Peptide Analog with amino acids located at positions 2, 5 and 8
      replaced by alanine (Ala).

<400> SEQUENCE: 19

Cys Ala Asp Pro Ala Ala Thr Ala Tyr Cys Arg Phe Phe Asn Ala Phe
 1               5                  10                  15

Cys Tyr Cys Arg Lys Leu
            20
```

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: AGRP
      Peptide Analog with amino acids located at positions 2, 3, 5 and 8
      replaced by alanine (Ala).

<400> SEQUENCE: 20

Cys Ala Ala Pro Ala Ala Thr Ala Tyr Cys Arg Phe Phe Asn Ala Phe
 1               5                  10                  15

Cys Tyr Cys Arg Lys Leu
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence:  AGRP
      Peptide Analog with amino acids located at positions 2, 5, 8, and
      11 replaced by alanine (Ala).

<400> SEQUENCE: 21

Cys Ala Asp Pro Ala Ala Thr Ala Tyr Cys Ala Phe Phe Asn Ala Phe
 1               5                  10                  15

Cys Tyr Cys Arg Lys Leu
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: AGRP
      Peptide Analog with amino acids located at positions 2, 5, 8, and
      12 replaced by alanine (Ala).

<400> SEQUENCE: 22

Cys Ala Asp Pro Ala Ala Thr Ala Tyr Cys Arg Ala Phe Asn Ala Phe
 1               5                  10                  15

Cys Tyr Cys Arg Lys Leu
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence:  AGRP
      Peptide Analog with amino acids located at positions 2, 5, 8, and
      13 replaced by alanine (Ala).

<400> SEQUENCE: 23

Cys Ala Asp Pro Ala Ala Thr Ala Tyr Cys Arg Phe Ala Asn Ala Phe
 1               5                  10                  15

Cys Tyr Cys Arg Lys Leu
            20

<210> SEQ ID NO 24
<211> LENGTH: 20
<212> TYPE: PRT
<213> ORGANISM: Artificial Sequence
<220> FEATURE:

<223> OTHER INFORMATION: Description of Artificial Sequence: AGRP
   Peptide Analog with amino acids located at positions 3, 6, and 17
   replaced by alanine (Ala) and in which the amino terminus is
   acetylated..

<400> SEQUENCE: 24

Asp Pro Ala Ala Thr Ala Tyr Cys Arg Phe Phe Asn Ala Phe Cys Tyr
 1               5                  10                  15

Ala Arg Lys Leu
        20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: ASP Peptide
   Analog in which amino acids located at positions 3, 4, 6, and 9
   are replaced by alanine (Ala).

<400> SEQUENCE: 25

Ala Cys Ala Ala Pro Ala Ala Ser Ala Gln Cys Arg Phe Phe Arg Ser
 1               5                  10                  15

Ala Cys Ser Cys Arg Val Leu
        20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: ASP Peptide
   Analog  in which amino acids located at positions 3, 6, and 17 are
   replaced by alanine (Ala) and the amino terminus is acetylated
   (Ac).

<400> SEQUENCE: 26

Asp Pro Ala Ala Ser Ala Gln Cys Arg Phe Phe Arg Ser Ala Cys Ser
 1               5                  10                  15

Ala Arg Val Leu
        20

<210> SEQ ID NO 27
<211> LENGTH: 144
<212> TYPE: DNA
<213> ORGANISM: Human

<400> SEQUENCE: 27
atgmgntgyg tnmgnytnca ygarwsntgy ytnggncarc argtnccntg ytgygayccn      60
tgygcnacnt gytaytgymg nttyttyaay gcnttytgyt aytgymgnaa rytnggnacn     120
gcnatgaayc cntgywsnmg nacn                                             144

<210> SEQ ID NO 28
<211> LENGTH: 96
<212> TYPE: DNA
<213> ORGANISM: Human

<400> SEQUENCE: 28
caygarwsnt gyytnggnca rcargtnccn gcngcngayc cngcngcnac ntgytaytgy      60
mgnttyttya aygcnttytg ytaygcnmgn aarytn                                96

<210> SEQ ID NO 29
<211> LENGTH: 96

<212> TYPE: DNA
<213> ORGANISM: Human

<400> SEQUENCE: 29
caygarwsnt gyytnggnca rcargtnccn gcngcngayc cngcngcnac ntgytaytgy    60
mgnttyttya aygcnttytg ytaygcnmgn aarytn                              96

<210> SEQ ID NO 30
<211> LENGTH: 96
<212> TYPE: DNA
<213> ORGANISM: Human

<400> SEQUENCE: 30
caygarwsng cnytnggnca rcargtnccn tgygcngayc cngcngcnac ngcntaytgy    60
mgnttyttya aygcnttytg ytaytgymgn aarytn                              96

<210> SEQ ID NO 31
<211> LENGTH: 96
<212> TYPE: DNA
<213> ORGANISM: Human

<400> SEQUENCE: 31
caygarwsnt gyytnggnca rcargtnccn tgygcngayc cngcngcnac ntgytaygcn    60
mgnttyttya aygcnttygc ntaytgymgn aarytn                              96

<210> SEQ ID NO 32
<211> LENGTH: 24
<212> TYPE: DNA
<213> ORGANISM: Human

<400> SEQUENCE: 32
tgymgnttyt tyaaygcntt ytgy                                           24

<210> SEQ ID NO 33
<211> LENGTH: 24
<212> TYPE: DNA
<213> ORGANISM: Human

<400> SEQUENCE: 33
tgymgnttyt tyggnwsngc ntgy                                           24

<210> SEQ ID NO 34
<211> LENGTH: 96
<212> TYPE: DNA
<213> ORGANISM: Human

<400> SEQUENCE: 34
tgygcngayc cntgygcnac ngcntaytgy mgnttyttya aygcnttytg ytaytgymgn    60
aarytnggna cngcnatgaa yccntgywsn mgnacn                              96

<210> SEQ ID NO 35
<211> LENGTH: 96
<212> TYPE: DNA
<213> ORGANISM: Human

<400> SEQUENCE: 35
gcngcngayc cntgygcnac ngcntaytgy mgnttyttya aygcnttytg ytaygcnmgn    60
aarytnggna cngcnatgaa yccntgywsn mgnacn                              96

<210> SEQ ID NO 36

<210> SEQ ID NO 36
<211> LENGTH: 96
<212> TYPE: DNA
<213> ORGANISM: Human

<400> SEQUENCE: 36
tgygcngayc cngcngcnac ngcntaytgy mgnttyttya aygcnttytg ytaytgymgn    60
aarytnggna cngcnatgaa yccngcnwsn mgnacn    96

<210> SEQ ID NO 37
<211> LENGTH: 96
<212> TYPE: DNA
<213> ORGANISM: Human

<400> SEQUENCE: 37
tgygcngayc cntgygcnac ngcntaygcn mgnttyttya aygcnttygc ntaytgymgn    60
aarytnggna cngcnatgaa yccntgywsn mgnacn    96

<210> SEQ ID NO 38
<211> LENGTH: 66
<212> TYPE: DNA
<213> ORGANISM: Human

<400> SEQUENCE: 38
tgygcngayc cngcngcnac ngcntaytgy mgnttyttya aygcnttytg ytaytgymgn    60 aarytn    66

<210> SEQ ID NO 39
<211> LENGTH: 96
<212> TYPE: DNA
<213> ORGANISM: Human

<400> SEQUENCE: 39
mgnaaywsnt gyaarccncc ngcnccngcn tgygcngayc cngcngcnws ntgycartgy    60
mgnttyttym gnwsngcntg ywsntgymgn gtnytn    96

<210> SEQ ID NO 40
<211> LENGTH: 93
<212> TYPE: DNA
<213> ORGANISM: Human

<400> SEQUENCE: 40
mgnaaywsnt gyaarccncc ngcnccngcn gcngayccng cngcnwsntg ycartgymgn    60
ttyttymgnw sngcntgyws ngcnmgngtn ytn    93

<210> SEQ ID NO 41
<211> LENGTH: 99
<212> TYPE: DNA
<213> ORGANISM: Human

<400> SEQUENCE: 41
mgnaaywsng cnaarccncc ngcnccngcn tgygcngayc cngcnwsngc nwsngcncar    60
tgymgnttyt tymgnwsngc ntgywsntgy mgngtnytn    99

<210> SEQ ID NO 42
<211> LENGTH: 69
<212> TYPE: DNA
<213> ORGANISM: Human

<400> SEQUENCE: 42
gcntgygcng ayccngcngc nwsngcncar tgymgnttyt tymgnwsngc ntgywsntgy    60

```
mgngtnytn                                                              69

<210> SEQ ID NO 43
<211> LENGTH: 78
<212> TYPE: DNA
<213> ORGANISM: Human

<400> SEQUENCE: 43
gcngcngayc cntgygcnws ngcncartgy mgnttyttym gnwsngcntg ywsngcnmgn      60
gtnytnwsny tnaaytgy                                                   78

<210> SEQ ID NO 44
<211> LENGTH: 78
<212> TYPE: DNA
<213> ORGANISM: Human

<400> SEQUENCE: 44
tgygcngayc cntgygcnws ngcncargcn mgnttyttym gnwsngcngc nwsntgymgn      60
gtnytnwsny tnaaytgy                                                   78

<210> SEQ ID NO 45
<211> LENGTH: 66
<212> TYPE: DNA
<213> ORGANISM: Human

<400> SEQUENCE: 45
tgygcngayc cngcngcnac ngcntaytgy mgnttyttya aygcnttytg ytaytgymgn      60 aarytn                                                                66

<210> SEQ ID NO 46
<211> LENGTH: 66
<212> TYPE: DNA
<213> ORGANISM: Human

<400> SEQUENCE: 46
tgygcngcnc cngcngcnac ngcntaytgy mgnttyttya aygcnttytg ytaytgymgn      60 aarytn                                                                66

<210> SEQ ID NO 47
<211> LENGTH: 66
<212> TYPE: DNA
<213> ORGANISM: Human

<400> SEQUENCE: 47
tgygcngayc cngcngcnac ngcntaytgy gcnttyttya aygcnttytg ytaytgymgn      60 aarytn                                                                66

<210> SEQ ID NO 48
<211> LENGTH: 66
<212> TYPE: DNA
<213> ORGANISM: Human

<400> SEQUENCE: 48
tgygcngayc cngcngcnac ngcntaytgy mgngcnttya aygcnttytg ytaytgymgn      60 aarytn                                                                66

<210> SEQ ID NO 49
<211> LENGTH: 66
<212> TYPE: DNA
```

<213> ORGANISM: Human

<400> SEQUENCE: 49
tgygcngayc cngcngcnac ngcntaytgy mgnttygcna aygcnttytg ytaytgymgn    60 aarytn    66

<210> SEQ ID NO 50
<211> LENGTH: 66
<212> TYPE: DNA
<213> ORGANISM: Human

<400> SEQUENCE: 50
tgygcngayc cngcngcnac ngcntaytgy mgnttyttya aygcnttytg ytaygcnmgn    60 aarytn    66

<210> SEQ ID NO 51
<211> LENGTH: 69
<212> TYPE: DNA
<213> ORGANISM: Human

<400> SEQUENCE: 51
gcntgygcng cnccngcngc nwsngcncar tgymgnttyt tymgnwsngc ntgywsntgy    60 mgngtnytn    69

<210> SEQ ID NO 52
<211> LENGTH: 54
<212> TYPE: DNA
<213> ORGANISM: Human

<400> SEQUENCE: 52
gayccngcng cnwsngcnca rtgymgntty ttymgnwsng cntgygcngt nytn    54

<210> SEQ ID NO 53
<211> LENGTH: 7
<212> TYPE: PRT
<213> ORGANISM: Artificial Sequence
<220> FEATURE:
<221> NAME/KEY: PEPTIDE
<222> LOCATION: (1)
<223> OTHER INFORMATION: Xaa in position 1 represents norleucine, a
      synthesic amino acid.
<220> FEATURE:
<221> NAME/KEY: PEPTIDE
<222> LOCATION: (1)
<223> OTHER INFORMATION: Description of Artificial Sequence: AGRP
      Peptide Analog

<400> SEQUENCE: 53

Xaa Gln His Phe Arg Trp Gly
 1               5

<210> SEQ ID NO 54
<211> LENGTH: 7
<212> TYPE: PRT
<213> ORGANISM: Artificial Sequence
<220> FEATURE:
<221> NAME/KEY: PEPTIDE
<222> LOCATION: (1)
<223> OTHER INFORMATION: Xaa in position 1 represents norleucine, a
      synthetic amino acid.
<220> FEATURE:
<223> OTHER INFORMATION: Description of Artificial Sequence: AGRP
      Peptide Analog

<400> SEQUENCE: 54

```
-continued

Xaa Asp His Phe Arg Trp Lys
 1               5

<210> SEQ ID NO 55
<211> LENGTH: 6
<212> TYPE: PRT
<213> ORGANISM: Artificial Sequence
<220> FEATURE:
<221> NAME/KEY: PEPTIDE
<222> LOCATION: (1)
<223> OTHER INFORMATION: Xaa in position 1 represents norleucine, a
      synthetic amino acid.
<220> FEATURE:
<223> OTHER INFORMATION: Description of Artificial Sequence: AGRP
      Peptide Analog

<400> SEQUENCE: 55

Xaa His Phe Arg Trp Lys
 1           5
```

I claim:

1. An isolated biologically active AGRP peptide selected from the group consisting of:
   (a) the peptide of any of SEQ ID Nos: 1–6, 8–12, and 19–24.

2. The peptide of claim 1 that is acylated at the amino terminus.

3. The peptide of claim 2 wherein an acetyl group is used for acylation.

4. A peptide selected from the group consisting of SEQ ID NOS:1–6, 8–12 and 18–24.

* * * * *

UNITED STATES PATENT AND TRADEMARK OFFICE
CERTIFICATE OF CORRECTION

PATENT NO. : 6,303,749 B1
DATED : October 16, 2001
INVENTOR(S) : Mark Anthony Jarosinski It is certified that error appears in the above-identified patent and that said Letters Patent is hereby corrected as shown below:

Column 6,
Line 63, change "utiLizes" to -- utilizes --.

Column 8,
Line 51, change "hemaglutiniri" to -- hemaglutinin --.

Column 28,
Table 11, Line 62, change "hMC3" to -- hMC4 --.

Column 29,
Line 35, change "Dphe" to -- dPhe --.

Signed and Sealed this

Third Day of August, 2004

JON W. DUDAS
*Acting Director of the United States Patent and Trademark Office*